(12) United States Patent
Song et al.

(10) Patent No.: US 7,863,388 B2
(45) Date of Patent: Jan. 4, 2011

(54) PREPARATION OF FUNCTIONALIZED CATIONIC POLYMERS AND THEIR APPLICATION IN PERSONAL CARE

(75) Inventors: Zhiqiang Song, Newtown, CT (US); John Jennings, Moycullen (IR); Jianwen Mao, Milford, CT (US)

(73) Assignee: BASF SE, Ludwigshafen (DE)

( * ) Notice: Subject to any disclaimer, the term of this patent is extended or adjusted under 35 U.S.C. 154(b) by 257 days.

(21) Appl. No.: 11/595,152

(22) Filed: Nov. 9, 2006

(65) Prior Publication Data

US 2007/0185281 A1    Aug. 9, 2007

Related U.S. Application Data

(60) Provisional application No. 60/736,608, filed on Nov. 14, 2005.

(51) Int. Cl.
    *C08F 36/14* (2006.01)
(52) U.S. Cl. .............. 525/328.3; 525/328.2; 525/328.4; 525/331.9; 525/332.1; 525/355; 525/359.1; 525/359.2; 525/359.3; 525/374; 525/375; 525/383; 526/258; 526/310; 510/102; 510/103; 510/119; 514/881; 514/772.1; 514/772.4; 514/772.5; 514/772.7
(58) Field of Classification Search .............. 525/328.2, 525/328.3, 359.1, 359.3, 379, 384, 385, 417, 525/540; 526/258, 310
    See application file for complete search history.

(56) References Cited

U.S. PATENT DOCUMENTS

| | | | | |
|---|---|---|---|---|
| 3,700,623 A | | 10/1972 | Keim et al. ............ 525/328.3 |
| 3,833,531 A | | 9/1974 | Keim et al. ................. 524/458 |
| 4,287,172 A | * | 9/1981 | Jacquet et al. ............... 424/47 |
| 4,341,887 A | | 7/1982 | Buriks et al. ................ 526/263 |
| 4,354,006 A | | 10/1982 | Bankert .................... 525/359.5 |
| 4,382,800 A | * | 5/1983 | Wang et al. ..................... 8/404 |
| 4,419,498 A | | 12/1983 | Bankert ..................... 525/426 |
| 4,419,500 A | | 12/1983 | Bankert ..................... 525/540 |
| 5,143,518 A | * | 9/1992 | Madrange et al. ............. 8/405 |
| 5,147,411 A | | 9/1992 | Töpfl ............................ 8/606 |
| 6,194,363 B1 | * | 2/2001 | Murray ....................... 510/119 |
| 6,203,785 B1 | * | 3/2001 | Holmes-Farley et al. . 424/78.18 |
| 6,323,306 B1 | * | 11/2001 | Song et al. .................. 528/342 |
| 6,416,627 B1 | * | 7/2002 | Cunkle et al. ............ 162/168.5 |

FOREIGN PATENT DOCUMENTS

JP    6-108382    4/1994

OTHER PUBLICATIONS

Trent, Propylene Oxide, Kirk-Othmer Encyclopedia of Chemical Technology, Jun. 4, 2001.*
Marshall, Chlorocarbons and Chlorohydrocarbons, Survey, Kirk-Othmer Encyclopedia of Chemical Technology, Apr. 18, 2003.*
English Language Abstract for JP6108382 printed from esp@cenet.com on May 7, 2007.

* cited by examiner

*Primary Examiner*—James Seidleck
*Assistant Examiner*—Robert C Boyle
(74) *Attorney, Agent, or Firm*—Shiela A. Loggins; Tyler A. Stevenson; Mervin G. Wood

(57) ABSTRACT

Water-soluble functionalized cationic copolymers obtainable by a process which comprises reacting a cationic base polymer which contains amino groups with at least one functional compound reactive to at least a part of the amino groups on the base polymer, are useful in personal care and cosmetic formulations.

12 Claims, No Drawings

PREPARATION OF FUNCTIONALIZED CATIONIC POLYMERS AND THEIR APPLICATION IN PERSONAL CARE

This application claims benefit under 35 USC 119(e) of provisional application No. 60/736,608, filed Nov. 14, 2005, the disclosure of which is hereby incorporated by reference.

The present invention is directed to functionalized water-soluble cationic polymers, methods to make them, and the use of compositions containing them in personal care applications.

BACKGROUND OF THE INVENTION

Cationic polymers have been used extensively in home and personal care, water treatment, papermaking, mineral processing, petroleum recovery, fabrics, and pharmaceuticals. Among the most important and extensively used cationic polymers are the quaternary ammonium polymers of diallyldialkyl ammonium compounds. In fact, polymers of diallyldimethyl ammonium chloride (DADMAC) are well known in the home and personal care industry as polyquaternium 6, and are used extensively in skin and hair care applications.

The use of homo- and copolymers of diallyldimethylammonium salts in hair care applications has been disclosed in several U.S. Patents.

Most of the currently available cationic polymers provide basic hair conditioning properties, but they also bring along some undesired attributes. One of these undesirable attributes is tackiness. This is also known as a sticky feeling of the polymer on the hair. This undesirable characteristic will cause the hair to clump, causing a decrease in hair volume. It may also weigh down the hair yielding a flattening effect.

The present invention relates to novel water-soluble and cationic copolymers, for example of diallyldimethylammonium chloride (DADMAC) and diallylamine (DAA), that provide excellent conditioning properties and improved tackiness. These copolymers overcome the tacky effect of the typical quaternary ammonium polymers of diallyldialkyl ammonium compounds (polyDADMAC). They also provide an excellent feel with less static fly away. They also contribute useful properties to skin care products.

U.S. Pat. Nos. 3,700,623 and 3,833,531 (assigned to Hercules Inc.) teach making certain acid stabilized poly(diallylamine)-epihalohydrin resins. In a first step a polymer of diallylamine (DAA) was prepared through radical polymerization using a radical initiator. The polymer of diallylamine was then reacted with an epihalohydrin, usually epichlorohydrin (ECH), at a temperature of from about 30 to 80° C. and at a pH of from 7 to 9.5 in aqueous solution. When the viscosity measured on a 20% to 30% solid solution reached a desired viscosity range (A to E on the Gardner-Holdt scale), the product was diluted with water to below 15% solids.

The obtained resin had a tendency to gel on standing. The resin solution was therefore stabilized against gelation by adding enough water-soluble acid (e.g. HCl) to adjust the pH to about 2. The acid-stabilized poly(diallylamine)-epichlorohydrin resins were reactivated prior to use by addition of a base (e.g. NaOH) to adjust pH to above 7. The half-reacted epihalohydrin entities of the alkaline curing resins impart epoxy functionality for crosslinking reactions after being reactivated by addition of alkaline base prior to use. These polymers are insoluble after crosslinking.

U.S. Pat. Nos. 4,354,006, 4,419,498 and 4,419,500 teach a process for making certain poly(DAA-ECH) polymers by reacting a diallylamine (DAA) polymer first with an allyl halide and then with hypohalous acid to convert the allyl substituents to halohydrin moieties.

JP 6,108,382 discloses another way to make certain poly(diallylamine)-epihalohydrin polymers. A diallylamine-epihalohydrin halo salt monomer is first prepared by reacting diallylamine with an epihalohydrin (typically epichlorohydrin) and then neutralizing with a halo acid (typically HCl). The DAA-ECH tertiary amine salt monomer is then polymerized using a radical initiator. The obtained poly(diallylamine)-epihalohydrin polymer is disclosed to provide excellent wet color fastness to a cellulose-based fiber dyed with a direct dye or a reactive dye.

U.S. Pat. No. 5,147,411 discloses a method to prepare the DAA-ECH monomers (3-halo-2-hydroxypropyl)diallylamine and (2,3-epoxypropyl)diallylamine, and their quaternary ammonium salts. The quaternary ammonium DAA-ECH salts are prepared by reacting a DAA-ECH tertiary amine with an alkyl sulfonate. The DAA-ECH quaternary ammonium salts are used directly in treating cellulose fiber material for improved color yield and wet-fastness of dyeing.

U.S. Pat. No. 4,341,887 discloses that the reaction product of diallylamine and epichlorohydrin (3-chloro-2-hydroxypropyl)diallylamine (a DAA-ECH monomer), can be converted to N,N-diallyl-3-hydroxy-azetidinium chloride (DAA-ECH azetidinium monomer) by heating in the presence of water. Removal of the solvent (water) by distillation or freeze drying causes the DAA-ECH azetidinium monomer to reconvert to the linear, non-quaternary N-3-chloro-2-hydroxypropyl-N,N-diallylamine. However (3-chloro-2-hydroxypropyl)diallylamine is not stable for long periods of time and dimerizes to 2,5-bis(diallylaminomethyl)-p-dioxane.

The azetidinium ring remains intact in the polymers obtained by free radical polymerization of the DAA-ECH azetidinium monomer. $_1$H NMR and $^{13}$C NMR were used to identify the azetidinium ring in the monomer and the polymers. The homo- and co-polymers of N,N-diallyl-3-hydroxyazetidinium are useful for demulsification, flocculation and floatation in water treatment.

The above-reviewed patents involve use of an epihalohydrin as a reactive compound to react with DAA monomer or a DAA polymer. Since an epihalohydrin (e.g. epichlorohydrin) is a difunctional reactive crosslinker, highly crosslinked insoluble end products are obtained when fully reacted with equivalent high DAA-containing (i.e. >5%) polymers. In the case where soluble cationic polymers are obtained, the polymers contain half reacted epichlorohydrin with potentially reactive epoxy groups. Only epihalohydrin is disclosed as a cross-linker for diallylamine polymers. Other polyfunctional compounds which could be used to crosslink the diallylamine polymers are not mentioned.

Commonly assigned U.S. Pat. No. 6,323,306, the disclosure of which is incorporated by reference, discloses a method to prepare certain water-soluble cationic polymers by reacting an amino-functionalized DADMAC polymer with a difunctional reactive crosslinker. The reactive crosslinkers include epihalohydrin and other polyfunctional compounds that can be used to cross-link the diallylamine polymers. The patent is limited to a DAA content of less than 5% to prevent formation of undesirable insoluble products which can be caused by excessive crosslinking due to use of the difunctional reactive crosslinker.

Commonly assigned U.S. Pat. No. 6,416,627, the disclosure of which is incorporated by reference, discloses polymeric light stabilizers which contain hindered amine nitroxide, hydroxylamine or hydroxylammonium salt groups, which stabilizers are useful for preventing loss of brightness and for enhancing resistance to yellowing in pulp or paper which still contains lignin. These polymers may be prepared by reacting a polymer containing pendant amino or hydroxyl groups, for example an amino-functionalized DADMAC polymer or a polyamine, with suitable hindered amine educts.

OBJECTS OF THE INVENTION

In the present invention a method of making certain functionalized cationic polymers useful in personal care and cosmetic applications by reacting at least one functional reactive compound with at least one water-soluble amino-group containing cationic base polymer which may be linear or branched and is optionally crosslinked. In one embodiment this may be for example a copolymer of diallyidimethylammonium chloride (DADMAC) and diallylamine (DAA).

A high degree of functionality (i.e. >5%) can be achieved by using monofunctional reactive compounds. A high degree of functionality (i.e. >5%) can also be achieved using a difunctional reactive compound, i.e. a crosslinker, for example by using a large excess of the difunctional reactive compound so that predominantly mono reaction and little crosslinking of the base polymer occurs.

The functionality of the functionalized cationic polymer of the present invention comes from the functional reactive compound used. Hydrophobic reactive compounds are preferably used to impart hydrophobicity to the base cationic polymer.

One object of the present invention is to provide certain functionalized or hydrophobically modified cationic copolymers, for example polyDADMAC-type copolymers, and methods for their preparation.

Another object of the invention is to provide personal care compositions and methods of use of functionalized or hydrophobically modified cationic copolymers, for example polyDADMAC-type copolymers, for example as additives to hair conditioners that enhance the feel, shine and many other properties of hair, or as additives to compositions for the skin.

Another object of the invention is to provide a personal care composition comprising at least one water-soluble functionalized cationic polymer obtainable by grafting an amino-group containing cationic base polymer with at least one compound which is reactive to the amino groups on the base polymer, at least one cosmetically-functional agent, and at least one cosmetically tolerable adjuvant.

The inventive polymers having hydrophobic/hydrophilic and cationic groups are able to enhance the substantivity of the polymer to keratinous substrates like hair, thereby improving the efficacy of a hair conditioner where it is most needed. At the same time, these polymers possess reasonable water solubility/dispersibility that can facilitate ease of use.

Another object of the invention is to provide personal care and cosmetic compositions, for example products for the skin and various forms of hair care products as aforementioned, wherein the performance of such products is further enhanced by incorporation of other additives such as perfumes, soil release polymers, colorants, preservatives, antimicrobials with activities against various microorganisms, optical brighteners, UV absorbers and other light management agents.

SUMMARY OF THE INVENTION

It has now been discovered that certain water-soluble functionalized cationic polymers can be made by reacting a water-soluble cationic base polymer, which may be linear or branched and is optionally crosslinked, and contains amino groups. with at least one compound which is reactive to the amino groups in the base polymer to impart the desired functionality. The reactive compound may be hydrophilic or hydrophobic, anionic, cationic, amphoteric or nonionic. In one embodiment at least one hydrophobic reactive compound is used as the grafting agent to impart hydrophobicity to the cationic base polymer.

Thus, in one aspect the present invention relates to a method of preparing a functionalized and/or hydrophobically modified cationic polymer which comprises, reacting a cationic base polymer, which may be linear or branched and is optionally crosslinked, and contains amino groups, with at least one functional compound, which may be hydrophobic or hydrophilic, anionic, cationic, amphoteric or nonionic, that can react with at least a part of the amino groups in the base polymer, with the proviso that the functional compound either does not contain hindered amine nitroxide, hydroxylamine or hydroxylammonium salt groups or, if such groups are present, at least a part of the amino-functional groups in the base polymer are also reacted, simultaneously or sequentially in any order, with at least one functional compound that does not contain hindered amine nitroxide, hydroxylamine or hydroxylammonium salt groups.

In another aspect the present invention relates to a functionalized and/or hydrophobically modified cationic polymer obtainable by reacting a cationic base polymer, which may be linear or branched and is optionally crosslinked, and contains amino groups, with at least one functional compound, which may be hydrophobic or hydrophilic, anionic, cationic, amphoteric or nonionic, that can react with at least a part of the amino groups in the base polymer, with the proviso that the functional compound either does not contain hindered amine nitroxide, hydroxylamine or hydroxylammonium salt groups or, if such groups are present, at least a part of the amino-functional groups in the base polymer are also reacted, simultaneously or sequentially in any order, with at least one functional compound that does not contain hindered amine nitroxide, hydroxylamine or hydroxylammonium salt groups.

The functionalized copolymers of the instant invention are prepared from cationic base polymers that contain sites suitable for grafting or cross-linking by added grafting and optionally cross-linking reagents. The functionalized water-soluble copolymers may be linear or branched and are optionally crosslinked.

Certain base polymers similar to those of the present invention have been disclosed previously, although heretofore the number of base polymer cross-linking sites has generally been so numerous and the crosslinker level used has been so high that the resulting polymers were cross-linked, mainly by epichlorohydrin, to an extent sufficiently high as to render them insoluble. Such insoluble resins are quite different in structure and in their intended application from the water-soluble base polymers employed herein.

According to the present invention, a high degree of functionality (>5 mole %) can be achieved without crosslinking the cationic base polymer, for example a poly-DADMAC-type cationic base polymer, by using a monofunctional reactive compound.

A water-soluble functionalized cationic polymer having a branched structure can be achieved with a difunctional reactive compound such as epichlorohydrin by controlling its incorporation into the base polymer at a low level (<5 mole %, preferably 1-3%). For example U.S. Pat. No. 6,323,306, the disclosure of which is incorporated by reference, discloses a method to prepare certain water-soluble cationic polymers by reacting an amino-functionalized DADMAC polymer with up to 3% of a difunctional reactive crosslinker. Such water-soluble crosslinked polymers are suitable as cationic base polymers which can be converted into water-soluble functionalized cationic polymers as taught herein. A water-soluble functionalized cationic polymer having a branched structure can also be achieved with a difunctional reactive compound by controlling the stoichiometric ratio of the base polymer and the reactive compound and/or the molecular weight of the base polymer used.

The grafted copolymers of the present invention provide exceptional conditioning properties on hair as well as enhancing the properties of skin care compositions.

In one embodiment the present invention is directed to a functionalized cationic copolymer comprising a main backbone obtainable by reacting:

(a) 0.1 to 99.9% by weight, preferably 20% to 99% by weight, of at least one cationic reactant according to formula (I)

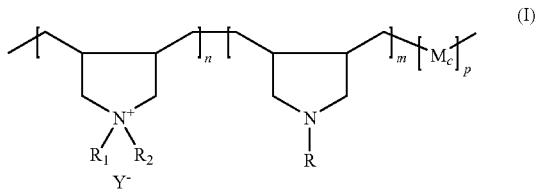

wherein R is hydrogen or $C_1$-$C_4$alkyl; $R_1$ and $R_2$ are, independently of each other, alkyl, hydroxyalkyl, carboxyalkyl, carboxamidoalkyl, or alkoxyalkyl groups having from 1 to 18 carbon atoms; $M_C$ represents a residue from an optional monomer (C) such as (meth)acrylamide or (meth)acrylate; n, m and p are the mole fractions of the repeating units in the corresponding brackets, respectively, of the cationic reactant of formula (I), m+n+p=1, and $Y^-$ represents an anion, with (b) 0.1 to 99.9% by weight of at least one functional compound (grafting agent), which may be hydrophobic or hydrophilic, anionic, cationic, amphoteric or nonionic, and is reactive to the attached amino groups on the backbone of the polymer of the formula (I), with the proviso that the functional compound either does not contain hindered amine nitroxide, hydroxylamine or hydroxylammonium salt groups or, if such groups are present in the functional compound, at least a part of the amino-functional groups in the base polymer are also reacted, simultaneously or sequentially in any order, with at least one functional compound that does not contain hindered amine nitroxide, hydroxylamine or hydroxylammonium salt groups.

Thus, in one embodiment the functionalized cationic polymers of the present invention may be represented by the formula

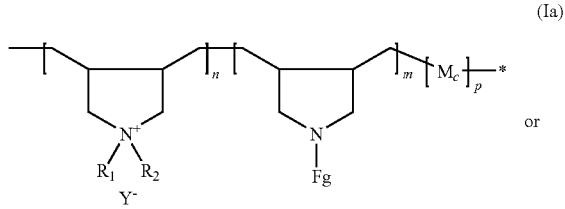

or

-continued (Ib)

wherein $R_1$ and $R_2$ are independently of each other, hydrogen, alkyl, hydroxyalkyl, carboxyalkyl, carboxamidoalkyl, or alkoxyalkyl having from 1 to 18 carbon atoms, $M_C$ represents a residue from an optional monomer C, and $Y^-$ represents an anion which can be inorganic or organic, Fg is the residue from at least one functional reactant grafted onto a cationic amino base polymer; $R_3$ is hydrogen, $C_1$-$C_4$alkyl or Fg; m, n and p are the mole fractions of the repeating units in the corresponding brackets, respectively, of the polymer of formula (Ia) or (Ib); m+n+p=1 and * is a terminal group, for example a catalyst residue, with the proviso that the functional residue Fg either does not contain hindered amine nitroxide, hydroxylamine or hydroxylammonium salt groups or, if such groups are present, at least a part of the amino-functional residue groups in the polymer have at least one functional residue that does not contain hindered amine nitroxide, hydroxylamine or hydroxylammonium salt groups.

In one embodiment the present invention is directed to personal care and cosmetic compositions comprising;
A) a polymeric functionalized cationic copolymer having a main backbone obtainable by reacting:

0.1 to 99.9% by weight, preferably 20% to 99% by weight, of at least one cationic reactant according to formula (I)

(I)

where R is hydrogen or $C_1$-$C_4$ alkyl; $R_1$ and $R_2$ are, independently of each other, alkyl, hydroxyalkyl, carboxyalkyl, carboxamidoalkyl, or alkoxyalkyl having from 1 to 18 carbon atoms; $M_C$ represents a residue from an optional monomer (C) such as (meth)acrylamide or (meth)acrylate; n, m and p are the mole fractions of the repeating units in the corresponding brackets, respectively, of the cationic reactant of formula (I), m+n+p=1, and $Y^-$ represents an anion, with 0.1 to 99.9% by weight of at least one reactive functional compound (grafting agent), which may be hydrophobic or hydrophilic, anionic, cationic, amphoteric or nonionic, and is reactive to the amino groups on the backbone of the polymer of the formula (I);
B) at least one cosmetically-functional agent, and
C) at least one cosmetically tolerable adjuvant.

Thus, in one embodiment of the personal care and cosmetic compositions, the functionalized cationic polymers of the present invention may be represented by the formulae

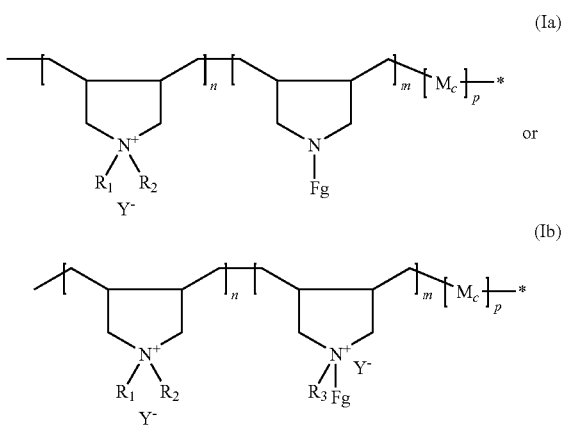

(Ia)

or (Ib)

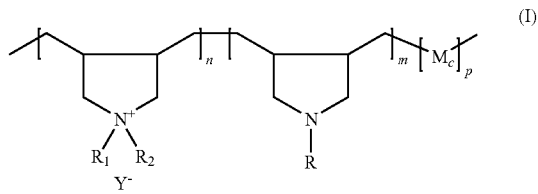

(I)

wherein $R_1$ and $R_2$ are independently of each other, hydrogen; alkyl, hydroxyalkyl, carboxyalkyl, carboxamidoalkyl, or alkoxyalkyl having from 1 to 18 carbon atoms, $M_C$ represents a residue from an optional monomer C, and $Y^-$ represents an anion which can be inorganic or organic, Fg is the residue from at least one functional reactant grafted onto a cationic amino-functional base polymer; $R_3$ is hydrogen, $C_1$-$C_4$ alkyl or Fg; m, n and p are the mole fractions of the repeating units in the corresponding brackets, respectively, of the polymer of formula (IIIa) or (IIIb) and * is a terminal group, for example a catalyst residue.

It should be clearly understood that the above formulae are idealized—in the actual polymers the various groups may be linked in any order. Thus both block and random copolymers are within the scope of the above formulae.

Many personal care compositions, for example, shampoos, soaps, etc., are washed away from the substrate after application. If one is to incorporate a conditioning agent into such compositions and wants the active ingredient to remain on the substrate after the rest of the formulation is washed away, it is important that the conditioning copolymer possesses excellent substantivity to the substrate. Since many of the substrates of concern, i.e. skin, hair, and nails, are hydrophobic and slightly anionic, a substance that is also hydrophobic, of higher molecular weight and catatonically charged would be preferred in order to impart the desired degree of substantivity to the substrate.

Other features of the present invention will be pointed out in the following description and examples, which disclose the principles of the invention and the best modes which are presently contemplated for carrying them out.

DETAILED DESCRIPTION OF THE INVENTION

One aspect of the present invention is directed to a method for making a functionalized water-soluble cationic polymer by reacting a cationic base polymer, which may be linear or branched and is optionally crosslinked, and contains amino groups, with at least one functional compound, which may be hydrophobic or hydrophilic, anionic, cationic, amphoteric or nonionic, that can react with at least a part of the amino groups in the base polymer, with the proviso that the functional compound either does not contain hindered amine nitroxide, hydroxylamine or hydroxylammonium salt groups or, if such groups are present, at least a part of the amino-functional groups in the base polymer are also reacted, simultaneously or sequentially in any order, with at least one functional compound that does not contain hindered amine nitroxide, hydroxylamine or hydroxylammonium salt groups.

In one embodiment the method comprises reacting an amino-functional cationic base polymer of the formula (I)

which may be linear or branched and optionally crosslinked, where R is hydrogen or $C_1$-$C_4$ alkyl; $R_1$ and $R_2$ are, independently of each other, alkyl, hydroxyalkyl, carboxyalkyl, carboxamidoalkyl, or alkoxyalkyl groups having from 1 to 18 carbon atoms; $M_C$ represents a residue from an optional monomer (C) such as (meth)acrylamide or (meth)acrylate, n, m and p are the mole fractions of the repeating units in the corresponding brackets, respectively, of the cationic reactant of formula (I); m+n+p=1, and $Y^-$ represents an anion, with at least one functional compound which can react with at least a part of the amino functional groups in the base polymer, with the proviso that the functional compound either does not contain hindered amine nitroxide, hydroxylamine or hydroxylammonium salt groups or, if such groups are present in the functional compound, at least a part of the amino-functional groups in the base polymer are also reacted, simultaneously or sequentially in any order, with at least one functional compound that does not contain hindered amine nitroxide, hydroxylamine or hydroxylammonium salt groups.

(A) Preparation of the Amino-Functionalized Base Polymer.

A quaternary ammonium cationic base polymer may be prepared by copolymerization of at least one quaternary ammonium cationic monomer (A), at least one copolymerizable monomer containing a reactive amine group (B), and optionally, at least one copolymerizable monomer (C) other than monomer A and monomer B, using a free radical initiator. The weight amount of monomer B may range from 0.05 to 99%, preferably from 0.2 to 50%, and the weight amount of monomer A plus monomer C may range from 99.9 to 0.05%, preferably from 99.8 to 50%. The weight ratio of monomer C to monomer A may vary from 0 to 3, and is preferably from 0 to 1.

Any quaternary ammonium cationic monomer may be used as monomer A. The cationic monomers useful in the practice of this invention include, but are not limited to, diallyldialkyl ammonium compounds, acryloxyethyl trimethyl ammonium chloride, methacryloxyethyl trimethyl ammonium chloride, vinyl benzyl trimethyl ammonium chloride, and 3-acrylamido-3-methyl butyl trimethyl ammonium chloride. The preferred cationic monomers for monomer A are diallyldialkyl ammonium compounds which may be represented by the formula A

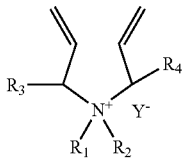

where $R_3$ and $R_4$ are, independently of each other, hydrogen or a $C_1$-$C_4$ alkyl group; $R_1$ and $R_2$ are, independently of each other, an alkyl, hydroxyalkyl, carboxy alkyl, carboxyamide alkyl or alkoxyalkyl group having from 1 to 18 carbon atoms; and $Y^-$ represents an anion. $R_3$ and $R_4$ are preferably hydrogen.

Examples of preferred cationic monomers include diallyldimethyl ammonium chloride (DADMAC), diallyidimethyl ammonium bromide, diallyldimethyl ammonium sulfates, diallyldimethyl ammonium phosphates, dimethallyl dimethyl ammonium chloride, diethylallyl dimethyl ammonium chloride, diallyl di(beta-hydroxyethyl ammonium chloride and diallyl di(beta-ethoxyethyl)ammonium chloride. The most preferred cationic monomer is DADMAC because of its commercial importance.

Preferred anions for $Y^-$ include, but are not limited to, chloride, bromide, sulfate, phosphate, nitrate, acetate, and tetrafluoroborate. Chloride is most preferred.

Any olefinic compound containing primary, secondary or tertiary amino functionality and copolymerizable with monomer A may be used as monomer B. The term "amino functionality" includes amine salts and oxides as well as the free amines.

Suitable compounds for monomer B include, but are not limited to, diallylamines, monoallylamines, dimethylaminoethyl(meth)acrylates, dimethylaminoethyl(meth)acrylamides, t-butylaminoethyl methacrylate, vinyl pyridine, and various amino styrenes such as p-dimethylaminomethyl styrene.

In one embodiment the amino monomer is a diallylamine represented by the formula B

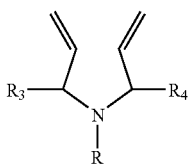

where R, $R_3$ and $R_4$ are, independently of each other, hydrogen or $C_1$-$C_4$ alkyl. R, $R_3$ and $R_4$ are preferably hydrogen.

Non-limiting examples of diallylamine monomers of formula B include, but are not limited to, diallylamine (DAA); 2,2'-dimethyl diallylamine; 2,2'-diethyl diallylamine; 2,2'-diisoprpyl diallylamine; 2,2'-dipropyl diallylamine; 2,2'-diisobutyl diallylamine; N-methyl diallylamine (MDAA); N-ethyl diallylamine; 2,2'-dimethyl-N-methyl diallylamine; 2,2'-diethyl-N-methyl diallylamine; 2,2'-diisoprpyl-N-methyl diallylamine; 2,2'-dipropyl-N-methyl diallylamine; 2,2'-dimethyl-N-ethyl diallylamine; and 2,2'-diethyl-N-ethyl diallylamine. DAA and MDAA are the most preferred.

Certain DADMAC/DAA copolymers are known from previously mentioned commonly assigned U.S. Pat. Nos. 6,323,306 and 6,416,627.

Suitable compounds for monomer C are olefinic monomers that are other than monomer A or monomer B. Non-limiting examples of such olefinic monomers include acrylamide, methacrylamide, N,N-dimethyl acrylamide N,N-diethyl acrylamide, N,N-dimethyl aminopropyl acrylamide and their salts; acrylic acid, methacrylic acid, vinyl sulfonic acid and their salts, vinyl pyrrolidone, hydroxyethylacrylate, vinyl amines, vinyl formamide, vinyl alcohol, vinyl caprolactam, vinyl derivatives of dimethyl siloxane, aminosiloxanes, vinyl fluorocarbons, hydroxyalkyl acrylates, 2-hydroxypropyl-acrylate, and 2-hydroxybutyl-acrylate; aminoalkyl acrylates such as N,N-dimethyl aminoethyl methacrylate, N,N-dimethyl aminoethyl acrylate, diethylaminoethyl acrylate and 7-amino-3,7-dimethyloctyl acrylate, and their salts including their alkyl and benzyl quaternized salts, and the like. Sulfur dioxide, while not an olefinic monomer, can also be a suitable compound for component C. (Meth)acrylamides and (meth)acrylates are preferred.

The copolymerization of monomers A, B and, optionally, monomer C to form the amino-functionalized cationic base polymer can be carried out by aqueous solution polymerization, water-in-oil inverse emulsion polymerization or dispersion polymerization using a suitable free radical initiator.

Examples of the suitable initiators include, but are not limited to, persulfates such as ammonium persulfate (APS); peroxides such as hydrogen peroxide, t-butyl hydroperoxide, and t-butyl peroxy pivalate; azo initiators such as 2,2'-azobis (2-amidinopropane) dihydrochloride, 4,4'-azobis-4-cyanovaleric acid and 2,2'-azobisisobutyronitrile, and redox initiator systems such as t-butyl hydroperoxide/Fe(II) and ammonium persulfate/bisulfite. Aqueous solution polymerization using ammonium persulfate (APS) is the preferred method for preparing the amino-functionalized base cationic polymer of the preferred monomers DADMAC and DAA (or MDAA).

The amount of the free radical initiator used in the polymerization process depends on the total monomer concentration and the type of monomers used, and may range from about 0.2 to about 5.0 wt % of total monomer charge to achieve more than 99% of total monomer conversion.

In one embodiment the polymerization is carried out in the substantial absence of oxygen. Oxygen can be removed from the reaction medium by applying vacuum with agitation or by purging with an inert gas such as nitrogen or argon. The polymerization can then be conducted under a blanket of the inert gas.

In one embodiment the amino-functionalized base polymer may be represented by formula (I)

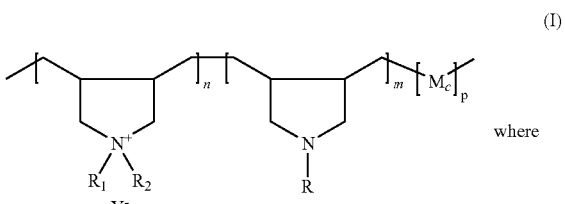

R is hydrogen or $C_1$-$C_4$ alkyl; $R_1$ and $R_2$ are, independently of each other, alkyl, hydroxyalkyl, carboxyalkyl, carboxamidoalkyl, or alkoxyalkyl groups having from 1 to 18 carbon atoms; $M_C$ represents a residue from at least one optional monomer C such as (meth)acrylamide or (meth)acrylate; n, m and p are the mole fractions of the repeating units in the corresponding brackets, respectively, of the cationic reactant of formula (I); m+n+p=1, and Y⁻ represents an anion.

(B) Functionalizing or Grafting the Base Polymer.

An amino-group containing base polymer (I) prepared for example as described above, is functionalized or modified by reacting it with at least one reactive functional compound (grafting agent and/or crosslinking agent) (II). Compounds with groups that can react with the amino-functional groups in the base polymer can be used to impart the properties or functionality of the grafting agent used. Suitable reactive compounds for grafting or crosslinking include, but are not limited to, epoxy compounds, haloalkyl compounds, isocyanate compounds and compounds containing activated olefinic double bonds. Suitable reactive compounds for grafting or crosslinking in non-aqueous systems also include acid halides and anhydrides.

In one embodiment of the invention, the functional reactive compound or grafting agent (II) used is an epoxy or halohydrin compound to give the functional group Fg as

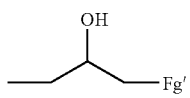

which contains a

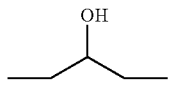

linkage connecting its residual Fg' to the amino nitrogen of the base polymer.

Examples of monofunctional epoxy compounds suitable for grafting include, but are not limited to, the following glycidyl compounds: mono-(2,3-epoxy)propylether-terminated polydimethyl-siloxanes, 3-glycidoxypropyltrimethoxysilane, 1-oxy-2,2,6,6,-tetramethyl-4-glycidyloxypiperidine, glycidyl isopropyl ether, glycidyl isobutyl ether, glycidyl heptyl ether, glycidyl 2-methylphenyl ether, glycidyl hexadecyl ether, glycidyl hexadecafluorononyl ether, glycidyl 4-nonylphenyl ether, 1,2-epoxydodecane, 1,2-epoxyoctadecane, 1,2-epoxy-3-phenoxy propane, glycidyltrimethylammonium chloride, glycidyl 3-nitrobenzenesulfonate, and the like.

Non-limiting examples of polyfunctional epoxy compounds include, but are not limited to, ethylene glycol diglycidyl either (EGDE); diglycidyl ether; 1,2,3,4-diepoxybutane; 1,2,5,6-diepoxyhexane; poly(propylene glycol) diglycidyl ether (PPGDE); 1,4-butanediol diglycidyl ether, 3-bis(glycidyloxy)methyl-1,2-propanediol, bisphenol A diglycidyl ether (BADGE), poly(phenyl glycidyl ether-co-formaldehyde), glycerol propoxylate tri-glycidyl ether, N,N-diglycidyl-4-glycidyloxyaniline, triglycidyl isocyanurate and the like. Preferred epoxy crosslinkers are bisphenol A diglycidyl ether and ethylene glycol diglycidyl ether.

When monofunctional epoxy compounds are reacted with a DAA copolymer of the formula (I'), functionalized cationic polymers such as those of the structure (IV) can be obtained:

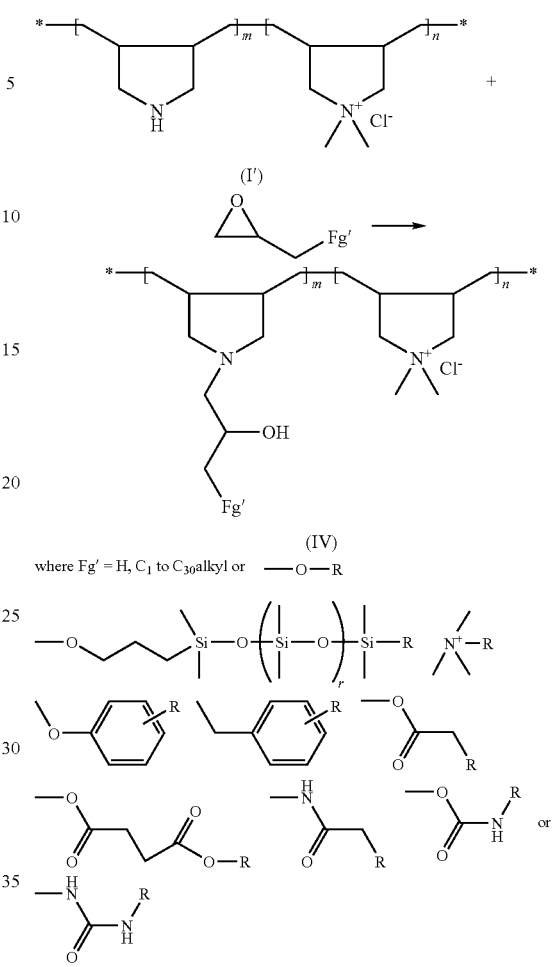

wherein R is hydrogen, C1 to C30 alkyl, C1 to C30 perfluoroalkyl, 1 to 1500 ethoxy units, 1 to 1500 propoxy units, 1 to 1500 mixed ethoxy-propoxy units, m and n are mole fractions of the repeating units within the corresponding brackets, with (m+n)=1, and r is a number from 1 to 100.

Certain epoxy compounds in halohydrin form can also be used as reactive compounds for functionalizing the amino cationic base polymer. Examples of these include, but are not limited to, 3-chloro-2-hydroxypropyl-dimethyldodecylammonium chloride and 3-chloro-2-hydroxypropyl-dimethyloctadecylammonium chloride (Quab® 342 & Quab® 426 from Degussa). Thus, in the functionalized cationic polymer of formula (IV), Fg' will be the residue from reacting 3-chloro-2-hydroxypropyl-dimethyldodecylammonium chloride or 3-chloro-2-hydroxypropyl-dimethylocta-decylammonium chloride.

Haloalkyl compounds can also be used as reactive compounds for functionalizing the base amino cationic polymer. Examples of mono-functional haloalkyl compounds suitable for grafting include, but are not limited to, chloroethane, bromoethane, 1-chloropropane, 1-chlorobutane, chloroacetic acid and its salts, dichloride-substituted cyanuric chloride and the like. Preferred haloalkyl reactants are bromoethane and chloroethane because of their low cost. Thus, in the functionalized cationic polymer of formula (Ia and Ib), Fg will be the residue of a haloalkyl compound to give the functional group Fg as

which contains a

linkage connecting its residual Fg' to the amine nitrogen of the base polymer (I).

The haloalkyl compound may also be a monovalent, perfluorinated, alkyl or alkenyl, linear, branched or cyclic organic radical having three to twenty fully fluorinated carbon atoms, which organic radical is optionally interrupted by divalent oxygen or sulfur atoms, and having a terminal iodo group. The perfluoroalkyl moiety may be a single perfluoroalkyl group, for example perfluorobutyl or perfluorohexyl, or a mixture of such groups, for example a mixture of $C_4F_9$—, $C_6F_{13}$—, $C_8F_{17}$—, $C_{10}F_{21}$—, $C_{12}F_{25}$— and $C_{14}F_{29}$— groups.

Perfluoroalkyl iodides $C_nF_{2n+1}$—I with n=4 to 14 are available from DuPont under the product names ZONYL® PFBI, ZONYL® TELA-L and ZONYL® TELA-N. They have the following average telomer distributions:

ZONYL® TEL PFBI: $C_4$=99.5% maximum;
ZONYL® TELA-L: $C_4$=4% maximum, $C_6$ 50=±3%, $C_8$ 29=±2%, $C_{10}$ 11=±2%, $C_{12}$=4±1%, $C_{14}$ and higher=2% maximum;
ZONYL® TELA-N: $C_6$=6% max., $C_8$ 50=±3%, $C_{10}$ 29=2%, $C_{12}$=11±1%, $C_{14}$ and higher=4% maximum, respectively.

Perfluoroalkylethyl iodides are also available from DuPont under the product names ZONYL® TELB-L, ZONYL® TELB and ZONYL® TELB-N. They have the following average telomer distributions:

ZONYL® TELB: $C_4$=4% maximum, $C_6$=35=±3%, $C_8$ 30=±3%, $C_{10}$ 17=±2%, $C_{12}$=8±1%, $C_{14}$ and higher=6% maximum;
ZONYL® TELB: $C_4$=4% maximum, $C_6$ 50=±3%, $C_8$29=±2%, $C_{10}$ 11=±2%, $C_{12}$=4±1%, $C_{14}$ and higher=2% maximum;
ZONYL® TELB-N: $C_6$=6% max, $C_8$ 50=±3%, $C_{10}$ 29=±2%, $C_{12}$=11±1%, $C_{14}$ and higher=4% maximum, respectively.

In one embodiment the functionalized cationic polymers of this invention may be synthesized by first reacting allyl glycidyl ether or a allyl halide with a primary or secondary amine on the cationic base polymer to introduce at least one allyloxy group, then adding an $R_F$-iodide to the resulting allyloxy radical, followed by partial or complete dehydrohalogenation. This is analogous to the reaction sequence taught in U.S. Pat. No. 6,706,923, the disclosure of which is incorporated by reference.

The addition of the perfluoroalkyl iodide to the allyloxy group may be carried out using methods and conditions similar to those disclosed for the addition of a perfluoroalkyl iodide to allyl alcohol in U.S. Pat. No. 5,585,517, the disclosure of which is incorporated by reference.

In another embodiment perfluoroalkylethyl iodides may also be added to a cationic base polymer backbone by first forming a perfluoroalkylethylene intermediate, which then adds to the amine groups on the polymer backbone as described in U.S. Pat. No. 6,365,676, the disclosure of which is incorporated by reference.

Examples of dihaloalkyl compounds that can be used to graft or crosslink cationic base polymers containing primary or secondary amino groups include, but are not limited to, 1,2-dichloroethane, 1,2-dibromoethane, 1,3-dichloropropane, 1,4-dichlobutane, 1,6-dichlorohexane, 1,10-dichlorodecane and the like. Preferred dihaloalkyl compounds are 1,2-dibromoethane and 1,2-dichloroethane.

Trihalo compounds such as cyanuric chloride and its chloro-substituted derivatives may also be employed. As is well known, replacement of each halogen on cyanuric chloride is progressively more difficult. This may be exploited to introduce dihalotriazinyl functional groups into a cationic base polymer, with subsequent reaction to introduce further functionality.

Examples of other difunctional reactants to graft or crosslink cationic base polymers include, but are not limited to, N,N'-methylenebisacrylamide (MBA), N,N'-ethylenebisacrylamide, epichlorohydrin, ethylene glycol diacrylate, diethylene glycol diacrylate, poly(ethylene glycol) diacrylate, poly(propylene glycol) diacrylate and the like. MBA is a preferred crosslinking agent.

Depending on the reactant charge ratio, one can preferentially react just one functional group of a difunctional reactant. When used as a crosslinker for the cationic base polymer, only low amounts (0.1 to 3 weight percent) will normally be employed.

Compounds containing activated olefinic double bonds can also be used to graft or crosslink cationic base polymers containing primary or secondary amino groups via a Michael addition. Examples of monofunctional compounds suitable for use in a Michael addition include, but are not limited to, (meth)acrylamide, (meth)acrylonitrile, esters of (meth) acrylic acid such as methyl acrylate, butyl acrylate, lauryl acrylate (LA), 2-hydroxyethyl acrylate (HEA), N-substituted (meth)acrylamides such as N,N-dimethylacrylamide and N-isopropylacrylamide (NIPA). Preferred compounds include 2-hydroxyethyl acrylate, N,N-dimethylacrylamide and N-isopropylacrylamide.

Thus, in the previously mentioned functionalized cationic polymers of formulae (Ia and Ib),

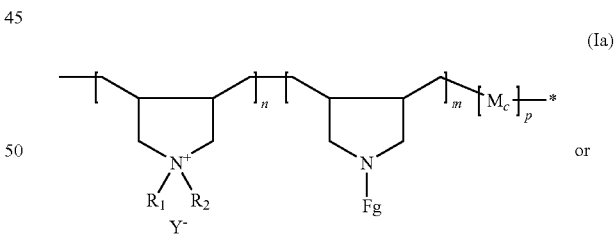

(Ia)

or

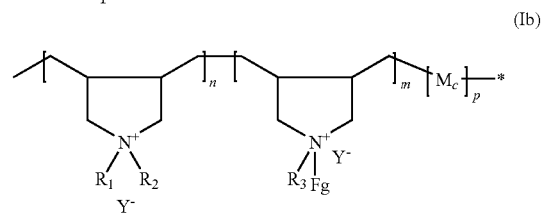

(Ib)

Fg will be the residue from reacting at least one compound containing an activated olefinic double bond, wherein said compound is an acrylate compound, to give the functional group Fg as

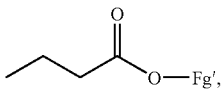

which contains a

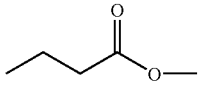

linkage connecting its residual Fg' to an amino nitrogen of a cationic base polymer.

When said compound is an acrylamide, it gives the functional groups Fg as

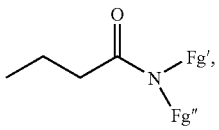

which contains a

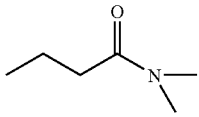

linkage connecting its residual Fg groups to an amino nitrogen of a cationic base polymer, wherein the Fg groups are the same or different.

When said compound is acrylonitrile or methacrylonitrile, it gives the functional group Fg as

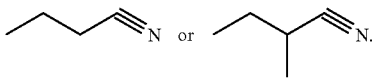

In one embodiment an isocyanate compound is grafted to a cationic base polymer containing primary or secondary amino groups. Examples of suitable isocyanate compounds include but are not limited to alkyl isocyanates such as isopropyl isocyanate, benzyl isocyanate, cyclohexyl isocyanate, dodecyl isocyanate, and other monofunctional isocyanates such as 3-(triethoxysilyl)propyl isocyanate, isocyanatoethyl methacrylate and the like. Examples of diisocyanate compounds include, but are not limited to, isophorone diisocyanate (IPDI), 1,4-diisocyanobutane, hexamethylene diisocyanate (HDI), toluene diisocyanate (TDI) and the like as well as diisocyanate compounds wherein one of the reactive groups is temporarily protected by an appropriate blocking agent. Preferred compounds include TDI, HDI, IPDi, etc.

Anhydride compounds can also graft to base polymers containing primary or secondary amino groups. Examples of suitable anhydride compounds for reactant (II) include, but are not limited to, phthalic, maleic, succinic, pyromellitic and tetrahydrophthalic anhydrides, 2-dodecen-1-yl succinic anhydride and the like. In one embodiment the anhydride compound is 2-dodecen-1-yl succinic anhydride.

The reactive compound is used in an amount ranging from about 0.02 to about 3.0 moles, preferably from 0.2 to 1.0 moles, of functional groups in the reactive compound for each mole of reactive amine present in the base polymer. The equivalent ratio of reactive compound to base polymer may change depending on the desired properties for the final polymer. The reactive compound is used in an amount which is effective to give a product certain desired properties after being fully reacted with the amino functional groups in the base polymer. More than one reactive compound may be reacted, simultaneously or sequentially in any order, with the base polymer.

The grafting reaction can be carried out in an aqueous medium or in the same reaction medium (e.g., water-in-oil emulsion) as is used for preparing the base polymer in step (a). The reaction is preferably carried out in aqueous medium at a pH of from about 7 to about 11, preferably from 7.5 to 9.5, and at a temperature from about 0 to about 100° C., preferably from 20 to 80° C. The solids concentration of the base polymer in the reaction medium prior to reaction can be, by weight, from 1% to about 60%, preferably from 10% to 25% for a solution of the base polymer, and preferably from 20 to 50% for an emulsion or dispersion of the base polymer.

In one embodiment the reactive compound is a hydrophobic reactant (II) which dissolves, at least in part, in the aqueous phase and is grafted onto the functional portion of the polymer backbone to form a polymer having both cationic and hydrophobic groups. When the hydrophobic reactant (II) is added to the polymer in an amount higher than its water solubility, the excess amount can form a second phase in the form of fine droplets if adequate agitation is provided. At the high reaction pH(>8), the amine groups in the cationic base polymer are not protonated and may form hydrophobic domains to absorb hydrophobic reactant (II) for grafting. The hydrophobic domains of the polymer will grow as the hydrophobic grafting progresses, accelerating transfer of hydrophobic reactant (II) to the reaction sites. The fine droplets of hydrophobic reactant (II) will eventually disappear after they are all transferred to the hydrophobic domain of the base polymer (I) for grafting.

Reactants with a functional group reactive to the amino groups in the base cationic polymer but also very reactive with water are preferably grafted in a non-aqueous solvent. In one embodiment the cationic base polymer is prepared in an aqueous solution. The aqueous solution of base polymer can then be dried to remove water and redissolved in a non-aqueous solvent for reacting with water-sensitive reactive compounds such as acid halides and anhydrides. Alternatively, a non-aqueous solvent can be added to the solution of the aqueous base polymer and the water removed by azeotropic distillation.

Examples of water-sensitive reactive compounds preferred for non-aqueous grafting include but are not limited to acid halides, anhydrides and isocynates. Since the reaction of an isocyanate with a primary or secondary amino group is much faster than with water, isocyanate compounds can also be reacted in an aqueous medium.

One embodiment of the present invention is a siloxane-modified polyDADMAC/DAA copolymer having the formula (V)

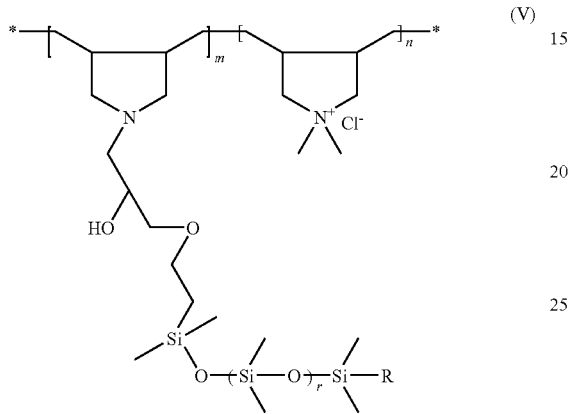

wherein R is an alkyl radical with 1 to 18 carbon atoms, preferably $C_4H_9$, m and n are the mole fractions of the repeating units in the corresponding brackets, respectively, of the polymer of formula (V), r is a number from 0 to 100 and * is a terminal group, for example a catalyst residue.

The siloxane functionality contained in the cationic copolymer of the formula (IV) imparts hydrophobicity to provide surface modification and other properties desired in personal care and other applications.

Another embodiment of the present invention is polyDADMAC copolymers with grafted antioxidant or UV absorbent functionality, such as those shown in the following partial formulae:

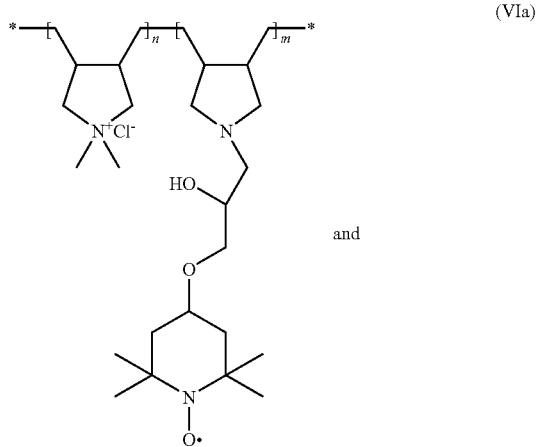

and

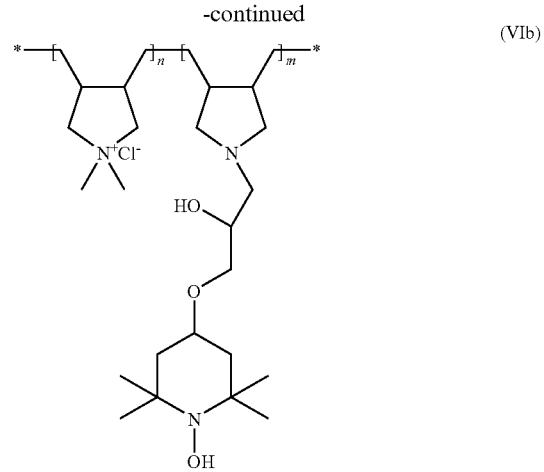

wherein m and n are the mole fractions of the repeating units in the corresponding brackets, respectively, of the polymers of formulae (Va) and (Vb) and * is a terminal group, for example a catalyst residue. As mentioned above, when hindered amine nitroxide, hydroxylamine or hydroxylammonium salt groups are present, at least one additional functional residue that does not contain hindered amine nitroxide, hydroxylamine or hydroxylammonium salt groups must also be present.

The molecular weight of the polymers of the present invention is not critical. It can range from 1,000 to 50,000,000, for example 10,000 to 5,000,000, and especially 20,000 to 2,000,000 Daltons, which can be a number or weight average molecular weight and can be determined by any commonly available method, such as light scattering, gel permeation chromatography, size exclusion chromatography, etc.

The polymers can be present in various physical forms, i.e. solutions, dispersions, suspensions, granules, powders, beads, blocks, etc. In the case of liquid forms such as solutions, dispersions, suspensions, etc., the liquid phase can be aqueous and/or non-aqueous such as a dispersion in soybean oil, an ester or mineral oil. Preferred hydrocarbons as the non-aqueous solvent or dispersion medium include, but are not limited to, naphthol spirits, Escaid 110 from Exxon, LPA 170 from Condea Vista and Conosol 200 from Penreco, an aromatics/paraffins/naphthalenes mixture.

The functionalized cationic polymers of the present invention as described above are found to be very useful in personal care compositions and more particularly in hair and skin care compositions. These compositions will generally comprise at least one cosmetically-functional agent used in an amount effective to impart desired cosmetic properties to the personal care composition.

The term "cosmetically-functional agent", as used herein, means any material, compound or composition applied to the hair or skin for a cosmetic effect. Exemplary cosmetically-functional agents include but are not limited to emollients, humectants, lubricants, UV-light absorbers, sunless tanning agents (e.g. DHA), antioxidants, free radical scavengers, preservatives, pigments, dye lakes, dyes, other colorants, aesthetic enhancers such as polysiloxanes and their various derivatives, rheology modifiers, natural polymers and their various derivatives and copolymers (e.g. starch, cellulosic polymers, gluccans, and their derivatives), perfumes and fragrances, film formers (water proofing agents), antiseptics, antifungal, antimicrobial and other medicaments, solvents, surfactants, natural or synthetic polymers, other conditioning agents and hair fixatives. Such cosmetically-functional agents also include mineral oils, glycerin, beeswax, lanolin, acetylated lanolin, stearic acid, palmitic acid, cetyl alcohol, sodium salts of olefin sulfonates, various proteins and derivatives, polymeric sugars, conditioning agents such as polyquaterniums and hair fixatives such as poly(vinyl pyrrolidone) and the copolymers of vinyl pyrrolidone with other monomers, and polyvinyl formamide.

The cosmetically-functional agent may be present in the personal care composition in an amount of from 0.01 to 60% by weight based on the total weight of the personal care composition.

In one embodiment the present invention is directed to a personal care composition comprising;

A) a polymeric functionalized cationic copolymer having a main backbone obtainable by reacting:

0.1 to 99.9% by weight, preferably 20% to 99% by weight, of at least one cationic reactant according to formula (I)

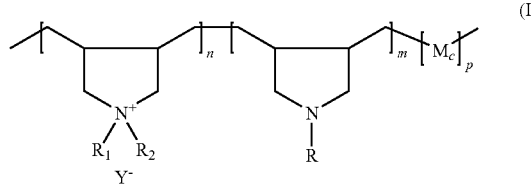

where R is hydrogen or $C_1$-$C_4$ alkyl; $R_1$ and $R_2$ are, independently of each other, alkyl, hydroxyalkyl, carboxyalkyl, carboxamidoalkyl, or alkoxyalkyl having from 1 to 18 carbon atoms; $M_C$ represents a residue from an optional monomer (C) such as (meth)acrylamide or (meth)acrylate; n, m and p are the mole fractions of the repeating units in the corresponding brackets, respectively, of the cationic reactant of formula (I), m+n+p=1, and $Y^-$ represents an anion, with 0.1 to 99.9% by weight of at least one reactive functional compound (grafting agent), which may be hydrophobic or hydrophilic, anionic, cationic, amphoteric or nonionic, and is reactive to the amino groups on the backbone of the polymer of the formula (I);

B) at least one cosmetically-functional agent, and

C) at least one cosmetically tolerable adjuvant.

The personal care composition according to the invention preferably comprises (A) from 0.01 to 15% by weight, for example from 0.5 to 10% by weight, based on the total weight of the composition, of at least one water-soluble functionalized cationic polymer obtained by reacting an amino-modified cationic base polymer with at least one functional compound which can react with the amino groups on the base polymer, and (B) from 0.01 to 60% by weight, for example 1 to 40% by weight, of at least one cosmetically-functional agent, and (C) the balance being at least one cosmetically tolerable adjuvant.

In one embodiment of the personal care preparation, the functionalized cationic polymers may be represented by the formulae

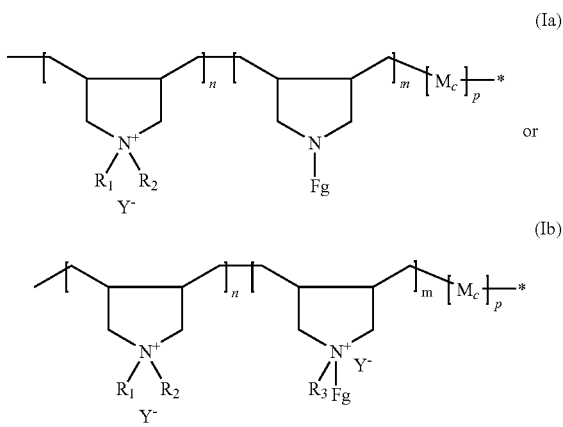

where $R_1$ and $R_2$ are independently of each other, hydrogen, alkyl, hydroxyalkyl, carboxyalkyl, carboxamidoalkyl, or alkoxyalkyl groups having from 1 to 18 carbon atoms, $M_C$ represents a residue from an optional monomer C, and $Y^-$ represents an anion which can be inorganic or organic, Fg is the residue from at least one functional reactant used to graft to a cationic amino-functional base polymer, $R_3$ is hydrogen, $C_1$-$C_4$ alkyl or Fg; m, n and p are the mole fractions of the repeating units in the corresponding brackets, respectively, of the polymer of formula (Ia) or (Ib) and * is a terminal group, for example a catalyst residue.

Personal care compositions include a very wide range of products. Suitable products include especially, but are not limited to, for example, cosmetic formulations for hair treatment, for example hair washes in the form of shampoos, hair conditioners, hair-care products, for example pretreatment products, hair tonics, hair styling creams and gels, pomades, hair rinses, deep conditioning treatments, intensive hair care treatments, hair setting products, for example waving agents for perms (hot wave, mild wave, cold wave), hair straightening or relaxing products, liquid hair fixatives, hair foams, hair sprays, bleaching agents, for example hydrogen peroxide solutions, bleaching shampoos, bleaching creams, bleaching powders, bleaching pastes or oils, temporary, semi-temporary or permanent hair dyes, products containing self-oxidizing dyes or natural hair dyes such as henna or chamomile, and mascaras.

They also include rinse off and leave on skin care products, for example softening, moisturizing and anti-wrinkle creams, lotions and gels; light-protective preparations such as sun tan lotions, creams and oils, sun blocks and pretanning and sunless tanning preparations; therapeutic compositions such as anti-acne and anti-psoriasis creams, gels and pastes, as well as skin coloring products such as facial make-up in the form of lipsticks, lip gloss, eye shadow, liquid make-up, day creams or powders, and facial lotions, creams and loose or pressed powders.

Personal care compositions may be in many different product forms, for example shampoos, bath- and shower additives, hair-care products, wax/fat compositions, liquid and solid soaps, lotions, gels, cremes, ointments, or other aqueous or alcoholic or aqueous/alcoholic solutions.

The personal care compositions listed above can be in a very wide range of physical forms of presentation, for example in the form of liquid formulations as an oil-in-water (O/W) emulsion,
in the form of a gel,
in the form of an oil, cream, milk or lotion,
in the form of a spray (spray with propellant or pump spray) or an aerosol,
in the form of a foam, or
in the form of a paste.

The choice of surface-active compound (surfactant) and the amount present in personal care formulations according to the invention will depend on the intended use of the composition. In personal care compositions, different surfactant systems may be chosen, as is well known to the skilled formulator. The total amount of surfactant present will also depend on the intended end use and may be as high as 60% by weight. Typically the compositions will comprise at least 2% by weight of surfactant, e.g. 2-60%, preferably 15-40% and most preferably 25-35%.

When the personal care composition is a liquid formulation in the form of an oil-in-water (O/W) emulsion, the oil component is preferably present in an amount of from 5 to 50 weight percent and more preferably from 10 to 35 weight percent based on the total weight of the personal care composition.

The emulsifiers may be used in an amount of, for example, from 1 to 30% by weight, preferably from 4 to 20-% by weight and especially from 5 to 10% by weight, based on the total weight of the personal care composition.

When formulated in O/W emulsions, the amount of the emulsifier system preferably represents 5% to 20% by weight of the oil phase.

In an O/W-formulation the oil phase (oil component) can be chosen from the following non-limiting substance groups:

Fatty Alcohols:
Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoates of $C_{12}$-$C_{15}$ alcohols, acetylated lanolin alcohol, etc.

Esters of Fatty Acids:
Esters of linear $C_6$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerization of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxo-synthesis and as monomer fractions in the dimerization of unsaturated fatty alcohols).

Examples of such ester oils are isopropyl myristate, isopropyl palmitate, isopropyl stearate, isopropyl isostearate, isopropyl oleate, n-butyl stearate, n-hexyl laurate, n-decyl oleate, isooctyl stearate, isononyl stearate, isononyl isononanoate, 2-ethylhexylpalmitate, 2-hexyllaurate, 2-hexyldecyl stearate, 2-octyldodecyl palmitate, oleyl oleate, oleyl erucate, erucyl oleate, erucyl erucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Further oil components that can be used are dicarboxylic acid esters, such as di(2-ethylhexyl)-2,6-naphthalate, di-n-butyl adipate, di(2-ethylhexyl)-adipate, di(2-ethylhexyl)-succinate and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups can also be used.

Natural or Synthetic Triglycerides Including Glyceryl Esters and Derivatives:
Di- or tri-glycerides based on $C_6$-$C_{18}$ fatty acids, modified by reaction with other alcohols (caprylic/capric triglyceride, wheat germ glycerides, etc.), fatty acid esters of polyglycerin (polyglyceryl-n such as polyglyceryl-4 caprate, polyglyceryl-2 isostearate, etc.) or castor oil (*Ricinus Communis*), hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc. can also be used.

Waxes:
This includes, but is not limited to, esters of long-chain acids and alcohols as well as compounds having wax-like properties, e.g., carnauba wax (Copernicia Cerifera), beeswax (white or yellow), lanolin wax, candellila wax (Euphorbia Cerifera), ozokerite, japan wax, paraffin wax, microcrystalline wax, ceresin, cetearyl esters wax, synthetic beeswax, etc.; also, hydrophilic waxes as cetearyl alcohol or partial glycerides.

Pearlescent Waxes:
This includes, but is not limited to, alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

This includes, but is not limited to, mineral oil (light or heavy), petrolatum (yellow or white), microcrystalline wax, paraffinic and isoparaffinic compounds, hydrogenated isoparaffinic molecules as polydecenes, and polybutene, hydrogenated polyisobutene, squalane, isohexadecane, isododecane and others from the plant and animal kingdoms.

Silicones or Siloxanes (Organosubstituted Polysiloxanes):

This includes, but is not limited to, dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form; linear polysiloxanes: dimethicones such as Dow Corning® 200 fluid, Mirasil® DM (Rhodia), dimethiconol; cyclic silicone fluids: cyclopentasiloxanes, volatiles such as Dow Corning® 345 fluid, Silbion® grade, Abil® grade; phenyltrimethicones; Dow corning® 556 fluid. Also suitable are simethicones, which are mixtures of dimethicones having an average chain length of from 200 to 300 dimethylsiloxane units with hydrogenated silicates. A detailed survey by Todd et al. of suitable volatile silicones may be found in addition in Cosm. Toil. 91, 27 (1976).

Fluorinated or Perfluorinated Oils.

This includes, but is not limited to, perfluorhexane, dimethylcyclohexane, ethylcyclopentane (Flutec® grades), and polyperfluoromethylisopropyl ether (Fomblin® grades).

Emulsifiers.

Any conventionally usable emulsifier can be used for the personal care compositions. Emulsifier systems may comprise for example:

carboxylic acids and their salts:

for example the salts of $C_8$-$C_{24}$, preferably $C_{14}$-$C_{20}$ saturated or unsaturated fatty acids, $C_8$-$C_{22}$ primary or secondary alkyl sulfonates, alkyl glycerol sulfonates, the sulfonated polycarboxylic acids described in published British Patent 1,082,179, paraffin sulfonates, N-acyl, N'-alkyl taurates, alkyl phosphates, isethionates, alkyl succinamates, alkyl sulphosuccinates, monoesters or diesters of sulfosuccinates, N-acyl sarcosinates, alkyl glycoside sulfates, polyethoxycarboxylates, the cation being an alkali metal (sodium, potassium, lithium), an unsubstituted or substituted ammonium residue (methyl, dimethyl, trimethyl, tetramethyl ammonium, dimethyl piperidinium, etc.) or a derivative of an alkanol amine (monoethanol amine, diethanol amine, triethanol amine, etc.);

sophorolipids, such as those in acid or lactone form, derived from 17-hydroxyoctadecenic acid, and sphingo- and glycolipids, such as those disclosed in WO 96/37192;

alkaline soaps of sodium, potassium and ammonium; metallic soaps of calcium or magnesium; organic basis soaps such as lauric, palmitic, stearic and oleic acid, etc., alkyl phosphates or phosphoric acid esters: acid phosphate, diethanolamine phosphate, potassium cetyl phosphate;

Examples of other anionic surfactants include: alkyl ester sulfonates of the formula

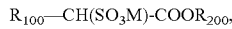

where $R_{100}$ is a $C_8$-$C_{20}$, preferably $C_{10}$-$C_{16}$ alkyl radical, $R_{200}$ is a $C_1$-$C_{16}$, preferably $C_1$-$C_3$ alkyl radical, and M is an alkaline cation (sodium, potassium, lithium), substituted or non-substituted ammonium (methyl, dimethyl, trimethyl, tetramethyl ammonium, dimethyl piperidinium, etc.) or a derivative of an alkanol amine (monoethanol amine, diethanol amine, triethanol amine, etc.);

alkyl sulfates of the formula $R_{300}OSO_3M$, where $R_{300}$ is a $C_5$-$C_{24}$, preferably $C_{10}$-$C_{18}$ alkyl or hydroxyalkyl radical, and M is a hydrogen atom or a cation as defined above, and their ethyleneoxy (EO) and/or propyleneoxy (P0) derivatives, having on average 0.5 to 30, preferably 0.5 to 10 EO and/or P0 units;

alkyl amide sulfates of the formula

where $R_{400}$ is a $C_2$-$C_{22}$, preferably $C_6$-$C_{20}$ alkyl radical, $R_{500}$ is a $C_2$-$C_3$ alkyl radical, and M is a hydrogen atom or a cation as defined above, and their ethyleneoxy (EO) and/or propyleneoxy (P0) derivatives, having on average 0.5 to 60 EO and/or P0 units.

The compositions of the invention may contain non-ionic surfactants. Nonionic surfactants that may be used include the primary and secondary alcohol ethoxylates, especially the $C_8$-$C_{20}$ aliphatic alcohols ethoxylated with an average of from 1 to 20 moles of ethylene oxide per mole of alcohol, and more especially the $C_{10}$-$C_{15}$ primary and secondary aliphatic alcohols ethoxylated with an average of from 1 to 10 moles of ethylene oxide per mole of alcohol. Non-ethoxylated nonionic surfactants include alkylpolyglycosides, glycerol monoethers, and polyhydroxyamides (glucamides).

Some particular examples of such nonionic surfactants include:

polyalkoxylenated alkyl phenols (i.e. polyethyleneoxy, polypropyleneoxy, polybutyleneoxy), the alkyl substituent of which has from 6 to 12 C atoms and contains from 5 to 25 alkoxylenated units; examples are TRITON X-45, X-114, X-100 and X-102 marketed by Rohm & Haas Co., and IGEPAL NP2 to NP17 made by Rhodia;

$C_8$-$C_{22}$ polyalkoxylenated aliphatic alcohols containing 1 to 25 alkoxylenated (ethyleneoxy, propyleneoxy) units; examples include TERGITOL 15-S-9, TERGITOL 24-L-6 NMW marketed by Dow, NEODOL 45-9, NEODOL 23-65, NEODOL 45-7, and NEODOL 454 marketed by Shell Chemical Co., KYRO EOB marketed by The Procter & Gamble Co., SYNPERONIC A3 to A9 made by ICI, RHODASURF IT, DB and B made by Rhodia;

the products resulting from the condensation of ethylene oxide or propylene oxide with propylene glycol and/or ethylene glycol, with a molecular weight in the order of 2,000 to 10,000, such as the PLURONIC products marketed by BASF;

the products resulting from the condensation of ethylene oxide and/or propylene oxide with ethylene diamine, such as the TETRONIC products marketed by BASF;

$C_8$-$C_{18}$ ethoxyl and/or propoxyl fatty acids containing 5 to 25 ethyleneoxy and/or propyleneoxy units;

$C_8$-$C_{20}$ fatty acid amides containing 5 to 30 ethyleneoxy units;

ethoxylated amines containing 5 to 30 ethyleneoxy units;

alkoxylated amidoamines containing 1 to 50, preferably 1 to 25 and in particular 2 to 20 alkyleneoxy (preferably ethyleneoxy) units;

amine oxides such as the oxides of alkyl $C_{10}$-$C_{18}$ dimethylamines, the oxides of alkoxy $C_8$-$C_{22}$ ethyl dihydroxy ethylamines;

alkoxylated terpene hydrocarbons such as ethoxylated and/or propoxylated α- or β-pinenes, containing 1 to 30 ethyleneoxy and/or propyleneoxy units;

alkylpolyglycosides obtainable by condensation (for example by acid catalysis) of glucose with primary fatty alcohols (e.g. those in U.S. Pat. Nos. 3,598,865 and 4,565, 647; and EP-A-132 043 and EP-A-132 046) having a $C_4$-$C_{20}$, preferably $C_8$-$C_{18}$ alkyl group and an average number of glucose units in the order of 0.5 to 3, preferably in the order of 1.1 to 1.8 per mole of alkylpolyglycoside (APG), particularly those having a $C_8$-$C_{14}$ alkyl group and on average 1.4 glucose units per mole, a $C_{12}$-$C_{14}$ alkyl group and on average 1.4 glucose units per mole, a $C_8$-$C_{14}$ alkyl group and on average 1.5 glucose units per mole or a $C_8$-$C_{10}$ alkyl group and on average 1.6 glucose units per mole, marketed under the names GLUCOPON 600 EC, GLUCOPON 600 CSUP, GLUCOPON 650 EC and GLUCOPON 225 CSUP respectively and made by Henkel;

It is preferred that the total level of non-ionic surfactants is from 0% by weight to 30% by weight, preferably from 1% by weight to 25% by weight, most preferably from 2% by weight to 15% by weight.

Another class of suitable surfactants comprises certain mono-long chain-alkyl cationic surfactants used in certain compositions similar to this invention. Cationic surfactants of this type include quaternary ammonium salts of the general formula $R_{10}R_{20}R_{30}R_{40}N^+X^-$ wherein the R groups are long or short hydrocarbon chains; typically alkyl, hydroxyalkyl or ethoxylated alkyl groups, and X is a counter-ion (for example, compounds in which $R_{10}$ is a $C_8$-$C_{22}$ alkyl group, preferably a $C_8$-$C_{10}$ or $C_{12}$-$C_{14}$ alkyl group, $R_{20}$ is a methyl group, and $R_{30}$ and $R_{40}$, which may be the same or different, are methyl or hydroxyethyl groups); and cationic esters (for example, choline esters).

Also useful are ethoxylated carboxylic acids or polyethylene glycol esters (PEG-n acylates), linear fatty alcohols having from 8 to 22 carbon atoms, products from 2 to 30 mol of ethylene oxide and/or from 0 to 5 mol propylene oxide with fatty acids having from 12 to 22 carbon atoms and with alkylphenols having from 8 to 15 carbon atoms in the alkyl group, fatty alcohol polyglycol ethers such as Laureth-n, Ceteareth-n, Steareth-n and Oleth-n, fatty acid polyglycol ethers such as PEG-n Stearate, PEG-n Oleate and PEG-n Cocoate;

monoglycerides and polyol esters; $C_{12}$-$C_{22}$ fatty acid mono- and di-esters of addition products of from 1 to 30 mol of ethylene oxide with polyols;

fatty acid and polyglycerol esters such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of these substance classes are also suitable. Fatty acid polyglycol esters such as monostearate diethylene glycol, fatty acid and polyethylene glycol esters; fatty acid and saccharose esters such as sucro esters, glycerol and saccharose esters such as sucro glycerides;

sorbitol and sorbitan: sorbitan mono- and di-esters of saturated and unsaturated fatty acids having from 6 to 22 carbon atoms and ethylene oxide addition products; polysorbate-n series, sorbitan esters such as sesquiisostearate, sorbitan, PEG-(6)-isostearate sorbitan, PEG-(10)-laurate sorbitan, PEG-17-dioleate sorbitan; glucose derivatives: $C_8$-$C_{22}$ alkyl-mono and oligo-glycosides and ethoxylated analogues with glucose being preferred as the sugar component; O/W emulsifiers such as Methyl Gluceth-20 sesquistearate, sorbitan stearate/sucrose cocoate, methyl glucose sesquistearate, cetearyl alcohol/cetearyl glucoside; also W/O emulsifiers such as methyl glucose dioleate/methyl glucose isostearate.

Sulfates and Sulfonated Derivatives:
Dialkylsulfosuccinates (e.g. DOSS, dioctyl sulfosuccinate), alkyl lauryl sulfonate, linear sulfonated paraffins, sulfonated tetrapropylene sulfonate, sodium lauryl sulfates, ammonium and ethanolamine lauryl sulfates, lauryl ether sulfates, sodium laureth sulfates, acetyl isothionates, alkanolamide sulfates such as taurines, methyl taurines, and imidazole sulfates;

Amine Derivatives:
These include amine salts, ethoxylated amines such as Oxide amine, amines with chains containing a heterocycle such as alkyl imidazolines, pyridine derivatives, isoquinolines, cetyl pyridinium chloride, cetyl pyridinium bromide, quaternary ammonium compounds such as cetyltrimethylammonium bromide, Stearylalkonium;

amide derivatives: alkanolamides such as acylamide DEA, ethoxylated amides, such as PEG-n acylamide, oxydeamide;

polysiloxane/polyalkyl/polyether copolymers and derivatives: dimethicone, copolyols, silicone polyethylene oxide copolymers and silicone glycol copolymers;

propoxylated or POE-n ethers (Meroxapols), Polaxamers or poly(oxyethylene)$_m$-block-poly(oxypropylene)$_n$-block (oxyethylene) copolymers;

zwitterionic surfactants that carry at least one quaternary ammonium group and at least one carboxylate and/or sulfonate group in the molecule. Zwitterionic surfactants that are especially suitable include the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines each having from 8 to 18 carbon atoms in the alkyl or acyl group and also cocoacylaminoethylhydroxyethylcarboxy-methylglycinate, N-alkyl-betaines and N-alkylaminobetaines;

alkylimidazolines, alkylopeptides and lipoaminoacids;
self-emulsifying bases (see K. F. DePolo—A Short Textbook Of Cosmetology, Chapter 8, Table 8-7, p 250-251);
non-ionic bases such as PEG-6 Beeswax (and) PEG-6 Stearate (and) polyglyceryl-2-isostearate [Apifac], Glyceryl stearate (and) PEG-100 stearate, [Arlacel 165], PEG-5 Glyceryl stearate [Arlatone 983 S], Sorbitan oleate (and) Polyglyceryl-3 Ricinoleate [Arlacel 1689], sorbitan stearate and sucrose cocoate [Arlatone 2121], Glyceryl stearate and laureth-23 [Cerasynth 945], cetearyl alcohol and Ceteth-20 [Cetomacrogol Wax], cetearyl alcohol and Polysorbate 60 and PEG-150 and stearate-20 [Polawax GP 200, Polawax NF], cetearyl alcohol and cetearyl polyglucoside [Emulgade PL 1618], cetearyl alcohol and Ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and Steareth-7 and Steareth-10 [Emulgator E 2155], cetearyl Alcohol and Steareth-7 and Steareth-10 [Emulsifying wax U.S.N.F], glyceryl stearate and PEG-75 stearate [Gelot 64], propylene glycol ceteth-3 acetate [Hetester PCS], propylene glycol isoceth-3 acetate [Hetester PHA], cetearyl alcohol and Ceteth-12 and Oleth-12 [Lanbritol Wax N 21], PEG-6 stearate and PEG-32 stearate [Tefose 1500], PEG-6 stearate and Ceteth-20 and Steareth-20 [Tefose 2000], PEG-6 Stearate and ceteth-20 and Glyceryl Stearate and steareth-20 [Tefose 2561], glyceryl stearate and Ceteareth-20 [Teginacid H, C, X];

anionic alkaline bases such as PEG-2 stearate SE, glyceryl stearate SE [Monelgine, Cutina KD] and propylene glycol stearate [Tegin P];

anionic acid bases such as cetearyl alcohol and sodium cetearyl sulfate [Lanette N, Cutina LE, Crodacol GP], cetearyl alcohol and sodium lauryl sulfate [Lanette W], Trilaneth-4 phosphate and glycol stearate and PEG-2 stearate [Sedefos 75], glyceryl stearate and sodium lauryl sulfate [Teginacid Special]; and cationic acid bases such as cetearyl alcohol and cetrimonium bromide.

Adjuvants and Additives:

The personal care compositions, for example creams, gels, lotions, alcoholic and aqueous/alcoholic solutions, emulsions, wax/fat compositions or ointments, may in addition contain, as further adjuvants and additives, mild surfactants, super-fatting agents, consistency regulators, additional thickeners, polymers, stabilizers, biologically active ingredients, deodorizing active ingredients, anti-dandruff agents, film formers, swelling agents, UV light-protective factors, antioxidants, hydrotropic agents, preservatives, insect repellents, solubilizers, perfume oils, colorants, bacteria-inhibiting agents and the like.

The adjuvants and additives may optionally be present in the personal care composition in an amount of, for example, from 0.1 to 25% by weight based on the total weight of the personal care composition.

Super-Fatting Agents:

Substances suitable for use as super-fatting agents include, for example, lanolin and lecithin and also polyethoxylated or acrylated lanolin and lecithin derivatives, polyol fatty acid esters, monoglycerides and fatty acid alkanolamides, the latter simultaneously acting as foam stabilizers.

Surfactants:

Examples of suitable mild surfactants, that is to say surfactants especially well tolerated by the hair, include fatty alcohol polyglycol ether sulfates, monoglyceride sulfates, mono- and/or di-alkyl sulfosuccinates, fatty acid isothionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Additional Thickeners and Rheology Modifiers:

Additional thickeners and rheology modifiers include silicon dioxide, magnesium silicates, aluminum silicates, polysaccharides or derivatives thereof, for example hyaluronic acid, xanthan gum, guar-guar, agar-agar, alginates, carraghenan, gellan, pectins, or modified celluloses such as hydroxycellulose and hydroxypropylmethylcellulose. In addition polyacrylates or homopolymers of reticulated acrylic acids and polyacrylamides, e.g. the Carbopol range (e.g. Carbopol types 980, 981, 1382, ETD 2001, ETD2020, Ultrez 10; INCI: Carbomer) or the Ciba Salcare® range such as Salcare® SC10, Salcare® SC11 and Salcare® SC Super 7 (all copolymers of acrylamide with diallyldimethylammonium chloride (DADMAC)), Salcare® SC30 (DADMAC homopolymer), Salcare® SC80 (Steareth-10 allyl ether/acrylates copolymer), Salcare® SC81 (acrylates copolymer), the Ciba Salcare® range of liquid dispersion polymers, which is a range of microparticulate acrylic-based polymeric thickeners in hydrophobic carrier mediums and includes Salcare® SC91 (sodium acrylates copolymer/PPG-1 trideceth-6/mineral oil), Salcare® SC92 (polyquaternium 32/mineral oil), Salcare/® SC95 (polyquaternium 37 in mineral oil with PPG-1 trideceth-6) and Salcare® SC96 (polyquaternium 37 in propylene glycol dicaprylate dicaprate with PPG-1 trideceth-6); Sepigel® 305 (polyacrylamide/laureth-7), Simulgel® NS and Simulgel® EG (hydroxyethyl acrylate/sodium acryloyidimethyl taurate copolymer), Stabilen® 30 (acrylates/vinyl isodecanoate crosspolymer), Pemulen® TR-1 (acrylates/$C_{10}$-$C_{30}$ alkyl acrylate crosspolymer), Luvigel® EM (sodium acrylates copolymer), Aculyn®28 (acrylates/beheneth-25 methacrylate copolymer), etc.

Polymers:

Suitable other cationic polymers include, for example, cationic cellulose derivatives, for example a quaternized hydroxymethyl cellulose obtainable under the name Polymer JR 400® from Amerchol, cationic starches, and acrylamides, quaternized vinylpyrrolidone/vinyl imidazole polymers, for example Luviquat® (BASF), condensation products of polyglycols and amines, quaternized collagen polypeptides, for example lauryldimonium hydroxypropyl hydrolyzed collagen (Lamequat® L/Grünau), quaternized wheat polypeptides, polyethyleneimine, cationic silicone polymers, for example amidomethicones, copolymers of adipic acid and dimethylaminohydroxypropyldiethylenetriamine (Cartaretin®/Clariant), copolymers of acrylic acid with dimethyldiallylammonium chloride (Merquat® 550/Chemviron), polyaminopolyamides, as described, for example, in FR-A-2 252 840, and the cross-linked water-soluble polymers thereof, cationic chitin derivatives, for example of quaternized chitosan, optionally distributed as microcrystals; condensation products of dihaloalkyls, for example dibromobutane, with bisdialkylamines, for example bisdimethylamino-1,3-propane, cationic guar gum, for example Jaguar® C-17 and Jaguar® C-16 from Celanese, quaternized ammonium salt polymers, for example Mirapol® A-15, Mirapol® AD-1, Mirapol® AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids cross linked with polyols, acrylamidopropyltrimethylammonium chloride/acrylate copolymers, acrylamidopropyltrimethyl-ammonium chloride/acrylamide copolymers (Ciba Salcare® SC60), octyl acrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethyl-aminoethyl methacrylate/vinyl caprolactam terpolymers and also optionally derivatized cellulose ethers and silicones. Furthermore the polymers as described in EP 1093796 (pages 3-8, paragraphs 17-68) may be used.

Biogenically Active Ingredients:

Biogenically active ingredients are to be understood as including, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorizing Active Ingredients.

Deodorizing active ingredients for skin care include, for example, antiperspirants, such as aluminum chlorohydrates (see J. Soc. Cosm. Chem. 24, 281 (1973)). Under the trade mark Locron® of Clariant, there is available commercially, for example, an aluminum chlorohydrate corresponding to formula $Al_2(OH)_5Cl \times 2.5H_2O$, the use of which is especially preferred (see J. Pharm. Pharmacol. 26, 531 (1975)). Besides the chlorohydrates, it is also possible to use aluminum hydroxyacetates and acidic aluminum/zirconium salts. Esterase inhibitors may be added as further deodorizing active ingredients. Such inhibitors are preferably trialkyl citrates, such as trimethyl citrate, tripropyl citrate, triisopropyl citrate, tributyl citrate and especially triethyl citrate (Hydagen® CAT, Henkel KGaA, Düsseldorf/GER), which inhibit enzyme activity and hence reduce odor formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Additional antibacterial active ingredients that influence the germ flora and kill or inhibit the growth of sweat-decomposing bacteria can likewise be present in the preparations. Examples include chitosan, phenoxyethanol and chlorhexidine gluconate. 5-Chloro-2-(2,4-dichlorophenoxy)-phenol (Irgasan® DP 300, Ciba Specialty Chemicals Corp.) has proved especially effective.

Anti-Dandruff Agents:

Anti-dandruff agents include, for example, climbazole, octopirox and zinc pyrithione.

Customary film formers include, for example, chitosan, microcrystalline chitosan, quaternized chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Antioxidants:

The personal care product can optionally contain one or more antioxidants. Any common antioxidant can be used. Typical examples of such antioxidants include 4,4'-di-alpha-cumyl-diphenylamine, mono- and dialkylated tert-butyl/tert-octyl-diphenylamines, n-octadecyl 3,5-di-tert-butyl-4-hydroxyhydrocinnamate, tetradibutyl pentaerythrityl-4-hydroxyhydrocinnamate, neopentanetetrayl tetrakis(3,5-di-tert-butyl-4-hydroxyhydrocinnammate), di-n-octadecyl-3,5-di-tert-butyl-4-hydroxybenzylphosphonate, 1,3,5-tris(3,5-di-tert-butyl-4-hydroxybenzyl)-isocyanurate, thiodiethylene bis(3,5-di-tert-butyl-4-hydroxyhydro-cinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3-tris-(2-methyl-4-hydroxy-5-tert-butyl-phenyl)butane, 1,3,5-tris[2-(3,5-di-tert-butyl-4-hydroxy-hydrocinnamoyloxy) ethyl] isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxy-benzylmercaptoacetate, bis(3,5-di-tert-butyl-4-hydroxyhydrocinnamoyl)-hydrazide, N,N'-bis[2-(3, 5-di-tert-butyl-4-hydroxyhydrocinnamoyloxy)-ethyl]oxamide, N,N-dialkylhydroxylamine, which may be prepared from di(hydrogenated tallow)amine by direct oxidation and sodium benzotriazolyl butylphenol sulfonate (Cibafast® H, Ciba Specialty Chemicals Corp.).

Further suitable antioxidants include amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. alpha-carotene, beta-carotene, lycopene) and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid, phytic acid, lactoferrin, alpha-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, alpha-glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]-sulfanilic acid (and salts thereof, for example the disodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide), and the derivatives (salts, esters, ethers, sugars, nucleotides, nucleosides, peptides and lipids) of HALS (="Hindered Amine Light. Stabilizer") compounds may also be mentioned.

The amount of antioxidants present is usually from 0.001 to 25 weight percent, preferably from 0.01 to 3 weight percent, based on the weight of the personal care product.

Hydrotropic Agents:

To improve the flow behavior of the compositions it is also possible to employ hydrotropic agents, for example ethoxylated or non-ethoxylated mono-alcohols, diols or polyols with a low number of C-atoms or their ethers (e.g. ethanol, isopropanol, 1,2-dipropanediol, propylene glycol, glycerin, ethylene glycol, ethylene glycol monoethyl ether, ethylene glycol monobutyl ether, propylene glycol monomethyl ether, propylene glycol monoethyl ether, propylene glycol monobutyl ether, diethylene glycol monomethyl ether; diethylene glycol monoethyl ether, diethylene glycol monobutyl ether and similar products). The polyols that come into consideration for this purpose preferably have from 2 to 15 carbon atoms and at least two hydroxy groups. The polyols may also contain further functional groups, especially amino groups, and/or may be modified with nitrogen. Typical examples include: glycerol, alkylene glycols, for example ethylene glycol, diethylene glycol, propylene glycol, butylene glycol, hexylene glycol and also polyethylene glycols having an average molecular weight of from 100 to 1000 Daltons; technical oligoglycerol mixtures having an intrinsic degree of condensation of from 1.5 to 10, for example technical diglycerol mixtures having a diglycerol content of from 40 to 50 weight percent; methylol compounds, such as, especially trimethylolethane, trimethylol-propane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; and dialcohol amines, such as diethanolamine or 2-amino-1,3-propanediol.

Preservatives and Bacteria-Inhibiting Agents:

Suitable preservatives include, for example, methyl-, ethyl-, propyl-, butyl-parabens, benzalkonium chloride, 2-bromo-2-nitro-propane-1,3-diol, dehydroacetic acid, diazolidinyl urea, 2-dichloro-benzyl alcohol, DMDM hydantoin, formaldehyde solution, methyldibromoglutanitrile, phenoxyethanol, sodium hydroxymethylglycinate, imidazolidinyl urea and triclosan, and further substance classes listed in the following reference: K. F. DePolo—A Short Textbook Of Cosmetology, Chapter 7, Tables 7-2, 7-3, 7-4 and 7-5, pp 210-219.

Bacteria-Inhibiting Agents:

Typical examples of bacteria-inhibiting agents are preservatives that have a specific action against gram-positive bacteria, such as 2,4,4'-trichloro-2'-hydroxydiphenyl ether (Ciba IRGASAN® DP 300), chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-trimethyl-2,6,10-dodecatrien-1-ol), which is present in lime blossom oil. Glycerol monolaurate has also proved to be a bacteriostatic agent.

The amount of the additional bacteria-inhibiting agents present is usually from 0.1 to 2 weight percent, based on the solids content of the preparations.

Perfume oils:

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (anis seed, coriander, caraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, scotch pine, mountain pine), from resins and balsams (galbanum, elemi, benzoin, myrrh, olibanum, opoponax). Animal raw materials also come into consideration, for example civet and castoreum. Typical synthetic aromatic substances include, for example, products of the ester, ether, aldehyde, ketone, alcohol or hydrocarbon types. Aromatic compounds of the ester type include, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol. Also alpha-hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, alpha-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat can be used alone or in admixture with one another.

Colorants:

There may be used as colorants any substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106 and similar publications in other countries, for example the CTFA and the FDA in the United States. The colorants are usually used in concentrations of from 0.001 to 0.1 weight percent, based on the total mixture.

Other Adjuvants:

It is furthermore possible for the personal care composition to contain, as adjuvants, antifoams, such as silicones, structurants such as maleic acid, solubilizers such as ethylene glycol, propylene glycol, glycerol or diethylene glycol, opacifiers such as latex, styrene/PVP or styrene/acrylamide copolymers, complexing agents such as EDTA, NTA, alaninediacetic acid or phosphonic acids, propellants such as propane/butane mixtures, fluorocarbons, $N_2O$, dimethyl ether, $CO_2$, $N_2$ or air, so-called coupler and developer components as oxidation dye precursors, reducing agents such as thioglycolic acid and derivatives thereof, thiolactic acid, cysteamine, thiomalic acid or mercaptoethanesulfonic acid, or oxidizing agents such as hydrogen peroxide, potassium bromate or sodium bromate.

For skin care there comes into consideration insect repellents, for example, N,N-diethyl-m-toluamide, 1,2-pentanediol or Insect Repellent 3535.

Ultraviolet Light Absorbers:

Ultraviolet Light Absorbers (UV absorbers) are employed in cosmetics to protect the product and/or substrate from chemical or physical deterioration induced by ultraviolet light. Sunscreen Agents are OTC drug ingredients, which protect from ultraviolet light. UV absorbers, like sunscreen agents, have the ability to convert incident ultraviolet radiation into less damaging infrared radiation (heat).

UV absorbers include, for example:

Acetaminosalol, allantoin PABA, benzalphthalide, benzophenone, Benzophenone-1, Benzophenone-2, Benzophenone-3, Benzophenone-4, Benzophenone-5, Benzophenone-6, Benzophenone-7, Benzophenone-8, Benzophenone-9, Benzophenone-10, Benzophenone-11, Benzophenone-12, benzotriazolyl dodecyl p-cresol, 3-benzylidene camphor, benzylidene-camphor hydrolyzed collagen sulfonamide, benzylidene camphor sulfonic acid, benzyl salicylate, bis-ethylhexyloxyphenol methoxyphenyl triazine, bornelone, bumetrizole, butyl methoxydibenzoylmethane, butyl PABA, Cibafast H, *Callophyllum Inophyllum* seed oil, *Camellia Sinensis* leaf extract, carotenoids, Ceria/Silica, Ceria/Silica talc, Cinoxate, DEA-methoxycinnamate, dibenzoxazoyl naphthalene, di-t-butyl hydroxybenzylidene camphor, diethylhexyl butamido triazone, diethylhexyl 2,6-naphthalate, digalloyl trioleate, diisopropyl methyl cinnamate, 1-(3,4-dimethoxyphenyl)-4,4-dimethyl-1,3-pentanediene, dimethyl PABA, ethyl cetearyidimonium tosylate, dimorpholinopyridazinone, diphenyl carbomethoxy acetoxy naphthopyran, disodium bisethylphenyl triaminotriazine stilbenedisulfonate, disodium distyrylbiphenyl disulfonate, disodium phenyl dibenzimidazole tetrasulfonate, Drometrizole, Drometrizole Trisiloxane, Esculin, ethyl dihydroxypropyl PABA, ethyl diisopropylcinnamate, ethylhexyl dimethoxybenzylidene dioxoimidazolidine propionate, ethylhexyl dimethyl PABA, ethylhexyl Ferulate, ethylhexyl methoxycinnamate, ethylhexyl salicylate, ethylhexyl triazone, ethyl methoxycinnamate, ethyl PABA, ethyl urocanate, Etocrylene, Ferulic Acid, 4-(2-beta-glucopyranosiloxy)propoxy-2-hydroxybenzophenone, glyceryl ethylhexanoate dimethoxycinnamate, glyceryl PABA, glycol salicylate, hexanediol salicylate, homosalate, hydrolyzed lupine protein, isoamyl p-methoxycinnamate, isopentyl trimethoxycinnamate trisiloxane, isopropylbenzyl salicylate, isopropyl dibenzoylmethane, isopropyl methoxycinnamate, menthyl anthranilate, menthyl salicylate, 4-methylbenzylidene camphor, methylene bis-benzotriazolyl tetramethylbutylphenol, octocrylene, octrizole, PABA, PEG-25 PABA, pentyl dimethyl PABA, phenylbenzimidazole sulfonic acid, *Pinus Pinaster* bark extract, polyacrylamidomethyl benzylidene camphor, Polysilicone-15, potassium methoxycinnamate, potassium phenylbenzimidazole sulfonate, red petrolatum, TINOSORB® M, TINOSORB® S and Cibafast® H (sodium benzotriazolyl butylphenol sulfonate, ex Ciba Specialty Chemicals Corp.), sodium isoferulate, sodium phenylbenzimidazole sulfonate, sodium urocanate, *Spirulina Platensis* Powder, TEA-phenylbenzimidazole sulfonate, TEA-salicylate, terephthalylidene dicamphor sulfonic acid, tetrabutyl phenyl hydroxybenzoate, titanium dioxide, tocotrienols, TriPABA Panthenol, urocanic acid, VA/crotonates/methacryloxybenzophenone-1 copolymer and *Vitis Vinifera* (grape) seed extract.

The following examples describe certain embodiments of this invention, but the invention is not limited thereto. It should be understood that numerous changes to the disclosed embodiments can be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

EXAMPLE 1

Synthesis of pDADMAC/DAA Copolymer

A 1-liter reactor equipped with a condenser, a thermometer, a nitrogen inlet and an overhead agitator is charged with 260 g of 66% DADMAC monomer, 34.5 g of diallylamine (DAA), 35.0 g of HCl solution, 6.0 g of deionized water, and 0.4 g of 20% Na$_4$EDTA solution. The polymerization mixture is purged with nitrogen and heated with agitation to a temperature of 80° C. An aqueous solution containing 2.1 g of ammonium persulfate (APS) is slowly fed to the reaction mixture over 190 minutes. The reaction temperature is allowed to increase to above 90° C. and then maintained at 90 to 100° C. during the APS feed period. After the APS feed, the reaction temperature is held at 95° C. for about 30 minutes. Then an aqueous solution containing 6 g of sodium metabisulfite (MBS) is added over 30 minutes. The reaction mixture is held at 95° C. for another 30 minutes to complete the polymerization (above 99% conversion). The polymer solution is then diluted with sufficient water to about 35% solids by weight and cooled to room temperature. The final product has a Brookfield viscosity of 9100 cps at 25° C. (using a Brookfield LV4 spindle at 30 rpms) and 33% polymer solids.

EXAMPLE 2

Following the same procedure as Example 1 the following polymers (in Table 1 below) are synthesized. The final product viscosities are measured at 25° C. using a Brookfield viscometer using a Brookfield LVT #3 spindle at 12 rpms. The viscosity results are shown in Table 1 below.

TABLE 1

| Sample | % DAA | % Solids | Viscosity (cps) |
| --- | --- | --- | --- |
| A | 19.5 | 41.8 | 4900 |
| B | 9.75 | 40.9 | 8100 |
| C | 4.8 | 36.9 | 4000 |
| D | 7.5 | 37.7 | 11000 |

EXAMPLE 3

A 0.5-liter reactor fitted with a mechanical stirrer, addition funnel and condenser is charged with 228.0 grams (0.129 mole secondary amine, NH) of the base polymer from Example 1. The reactor content is adjusted with 6.0 g of 25% NaOH aqueous solution to a pH of 9.0 to 10.0 and heated to 70° C. with agitation. After the pH adjustment, 7.6 g (0.0076 mole epoxide) of mono-(2,3-epoxy)propyl ether-terminated polydimethylsiloxane (MCR-E11 from the Gelest) is added into the reactor. The grafting reaction is maintained at about 70° C. and the viscosity of the reaction solution is monitored with an agitator torque meter. The viscosity of the reactor contents, as is indicated by the torque meter reading, increases with reaction time. The viscosity increase is believed to result from association of grafted hydrophobic siloxane groups and can be an indication of the grafting reaction. While the viscosity shows little further increase with increasing reaction time after about four hours, the reaction mixture is held at 70° C. for another 2 hours. A concentrated HCl solution and deionized water are added to adjust the pH to about 5 and the solids. The resulting polymer product is a homogeneous, yellowish emulsion-looking solution having 20.0 weight percent of polymer solids (base polymer Ia+grafting agent II) and a Brookfield viscosity of about 1200 cps (using a Brookfield LV3 spindle at 30 rpms at 25° C.). The functionalized cationic polymer contains about 10 weight percent of grafted MCR-E11, which provides hydrophobic siloxane functionality to the copolymer.

EXAMPLE 4

The procedure of Example 3 is followed except that 18.1 g instead 7.6 g of MCR-E11 grafting agent is added. The resulting polymer product is a homogeneous, yellowish emulsion-looking solution with 20.0 weight percent of polymer solids (base polymer I+grafting agent II) and a Brookfield viscosity of about 1200 cps (using a Brookfield LV3 spindle at 30 rpms at 25° C.). The copolymer contains about 20 weight percent of grafted MCR-E11 which provides substantial hydrophobic siloxane functionality to the cationic copolymer.

EXAMPLE 5

A 1-liter reactor fitted with a mechanical stirrer, addition funnel and condenser is charged with 250 grams of 22.1 weight percent base polymer from Example 1 (0.096 mole secondary amine, NH). 6.0 g of a 25% NaOH solution is added to bring the pH above 9.0. The reactor contents are diluted with 26.2 g of deionized water, and then 10.0 g of 2-hydroxyethyl acrylate (HEA, 97%) is added at a temperature of about 20° C. The reaction is monitored by following the disappearance of HEA via liquid chromatography (HPLC). The grafting reaction is terminated after more than 95% of the added HEA has reacted. The reaction causes an increase in viscosity. Deionized water is added from time to time during the reaction to maintain a suitable reaction viscosity for agitation. The resulting product is a clear solution containing 11.5 weight percent of the grafted polymer solids. The polymer solids contain about 15 weight percent of grafted HEA units which adds hydroxyl functionality to the cationic pDADMAC/DAA copolymer.

EXAMPLE 6

1.8 g of acrylamide (50%) solution is added to 25 g of the product from Example 1 after the pH is adjusted to 9.0 with a 25% NaOH solution. After thorough mixing the solution is allowed to react at 23 to 26° C. for about three days. The solution viscosity increases from an initial 7720 cps to 16,320 cps after the reaction. The resulting polymer solution is clear and contains 31.2 weight percent polymer solids. The obtained cationic copolymer has about 15 weight percent of grafted acrylamide units which adds the functionality of pendant amide groups to the cationic pDADMAC/DAA copolymer.

EXAMPLE 7

50 g (428 mmol) of methoxypolyethylene glycol 350 (MPEG 350-Dow chemical) is placed into a round-bottomed flask equipped with a stirrer, nitrogen inlet and a thermoregulator and heated with stirring. When the temperature reaches 65° C., 1.6 g of boron trifluoride etherate is added to the flask. Then 35.7 g (386 mmol) of epichlorohydrin is added drop-wise to the flask over 1 hour. An exotherm is observed with an increase in temperature from 65° C. to 74° C. When the rise in temperature subsides, the reaction mixture is maintained at 65° C. for three hours with stirring. At this time the consumption of epichlorohydrin is determined to be complete by gas chromatography. Next 30.8 g of a 50% NaOH solution is added to the mixture, which is then stirred at 60° C. for one hour. Formation of epoxy groups is monitored by gas chromatography and chloride ion titration. The mixture is then extracted using diethyl ether to separate the product from water and salts. This intermediate is obtained as a clear amber liquid.

EXAMPLES 8-28

50.0 g (20.5 mmol/eq. wt. based on DAA in sample) of the base polymer B from Example 2 is diluted with 20 g of deionized water. The pH is adjusted with 1.2 g of a 50% NaOH solution. 1.2 g (6.2 mmol) of 1-oxy-2,2,6,6,-tetramethyl-4-glycidyloxypiperidine (glycidol TEMPO) is added to the solution. After thorough mixing, the reaction mixture is allowed to react at 70° C. for 5 hours. After this time the consumption of 1-oxy-2,2,6,6,-tetramethyl-4-glycidyloxypiperidine (glycidol TEMPO) is determined to be >99% by liquid chromatography. 50 g of deionized water is added along with 0.5 g of 50% NaOH solution. When the temperature reaches 70° C., 5.5 g (6.2 mmol) of a 38% solution of 3-chloro-2-hydroxypropyl-dimethyldodecylammonium chloride (Quab® 342 from Degussa) and 5 g of 2-propanol are added to the flask. The reaction mixture is maintained at 70-75° C. for three hours with stirring. During the reaction 20.0 g of deionized water is added to aid in viscosity control. The mixture is then analyzed for the consumption of Quab 342 using liquid chromatography. Also the hydrolysis of the Quab 342 to Glycol is monitored by titration and using liquid chromatography. After this time the mixture is cooled to room temperature and 116 g of deionized water and 1.4 g of concentrated HCl is added to adjust the pH. The modified poly-DADMAC copolymer is obtained as a clear viscous yellow mixture of 9.1 wt. % solids. The cationic polymer contains about 4.4 weight % of grafted glycido TEMPO which provides antioxidant functionality from the pendant nitroxyl groups and 7.7 wt % of the 3-chloro-2-hydroxypropyl-dimethyldodecylammonium chloride reaction product.

Table 2 summarizes the properties of the above polymer and others prepared analogously.

TABLE 2

| Example | Polymer | Grafted component 1 (Mol ratio[1]) | Grafted component 2 (Mol ratio[1]) |
|---------|---------|-----------------------------------|-----------------------------------|
| 8  | B | Glycidol TEMPO (0.3) | Quab 342 (0.3) |
| 9  | A | Glycidol TEMPO (0.5) | Quab 342 (0.5) |
| 10 | B | Glycidol TEMPO (0.1) | Quab 342 (0.1) |
| 11 | A | Glycidol TEMPO (0.5) | Quab 151 (0.5) |
| 12 | C | Glycidol TEMPO (0.2) | Quab 151 (0.2) |
| 13 | D | Glycidol TEMPO (0.4) | Quab 151 (0.4) |
| 14 | B | Glycidol TEMPO (0.3) | Quab 426 (0.3) |
| 15 | A | Glycidol TEMPO (0.5) | Quab 426 (0.5) |
| 16 | A | Glycidol TEMPO (0.3) | Quab 426 (0.3) |
| 17 | A | Glycidol TEMPO (0.1) | Quab 426 (0.1) |
| 18 | D | Glycidol TEMPO (0.4) | E-dodecane (0.4) |
| 19 | D | Glycidol TEMPO (0.1) | E-dodecane (0.1) |
| 20 | B | Glycidol TEMPO (0.4) | E-hexane (0.4) |
| 21 | B | Glycidol TEMPO (0.2) | E-hexane (0.2) |
| 22 | B | Glycidol TEMPO (0.4) | PGE (0.4) |
| 23 | C | Glycidol TEMPO (0.5) | PSA (0.5) |
| 24 | D | Glycidol TEMPO (0.3) | CA (0.6) |
| 25 | A | Glycidol TEMPO (0.4) | PEG 350 (0.4) |
| 26 | A | Glycidol TEMPO (0.5) | Dodecenyl SA (0.5) |
| 27 | C | Glycidol TEMPO (0.5) | Succinic Anhydride (0.5) |
| 28 | A | Glycidol TEMPO (0.4) | Phthalic Anhydride (0.4) |

[1]Based on diallylamine content
Glycidol TEMPO = 1-oxy-2,2,6,6,-tetramethyl-4-glycidyloxypiperidine
Quab 342 = 3-chloro-2-hydroxypropyl-dimethyldodecylammonium chloride
Quab 151 = glycidyltrimethylammonium chloride
Quab 426 = 3-chloro-2-hydroxypropyl-dimethyloctadecylammonium chloride
E-Dodecane = 1,2-epoxydodecane
E-Hexane = 1,2-epoxyhexane
PGE = Phenyl glycidyl ether
PSA = 3-chloro-2-hydroxy-1-propane sulfonic acid, Na salt.
CA = 2-Chloroacetamide
PEG 350 = Carbowax 350 = polyethylene glycol 350
Dodecenyl SA = 2-Dodecen-1-yl succinic anhydride

EXAMPLES 29-49

50.0 g (42 mmol/eq. wt. based on DAA in sample) of the base polymer A from Example 2, 10.1 g of deionized water and 3.3 g 50% NaOH solution are placed into a round-bottomed flask equipped with a stirrer, nitrogen inlet and a thermoregulator and heated. When the temperature reaches 70° C., 30.2 g (33.5 mmol) of a 38% solution of 3-chloro-2-hydroxypropyl-dimethyldodecylammonium chloride (Quab 342 from Degussa) and 8 g of 2-propanol are added to the flask. An exotherm is observed with an increase in temperature from 65° C. to 70° C. When the rise in temperature subsides, the reaction mixture is maintained at 65° C. for three hours with stirring. During the reaction 6.0 g of deionized water is added to aid in viscosity control. At this time the consumption of Quab 342 is determined to be >99% by chloride titration. Also the hydrolysis of the Quab 342 to Glycol is monitored by titration and using liquid chromatography. After this time the mixture is cooled to room temperature and 179 g of deionized water and 1.5 g of a 2.3% HCl/water solution is added to adjust the pH. The modified polyDADMAC copolymer is obtained as a clear viscous yellow mixture of 12.8 wt. % solids.

The final product has a Brookfield viscosity of 4900 cps at 25° C. (using a Brookfield LV3 spindle at 12 rpms) at 12.8% polymer solids.

Table 3 summarizes the properties of the above polymer and others prepared analogously.

TABLE 3

| Example | Base Polymer | Grafted component (Mol ratio[1]) | Viscosity (cps) | Solids, wt. % | Appearance |
|---|---|---|---|---|---|
| 29 | A | Quab 342 (0.8) | 4900[2] | 12.8 | Opaque liquid |
| 30 | A | Quab 342 (0.4) | 8100[3] | 12.6 | Opaque liquid |
| 31 | B | Quab 342 (0.8) | 4000[4] | 13.5 | Clear slightly yellow gel |
| 32 | B | Quab 342 (0.4) | 1100[4] | 13.0 | Clear slightly yellow gel |
| 33 | A | Quab 151 (0.3) | — | 7.2 | Clear yellow liquid |
| 34 | A | Quab 151 (0.8) | — | 8.3 | Clear yellow liquid |
| 35 | A | Quab 426 (0.8) | — | 22.2 | Opaque gel |
| 36 | A | Quab 426 (0.4) | 1250[5] | 12.8 | Opaque gel |
| 37 | C | Quab 426 (0.8) | 1800[2] | 12.2 | Clear slightly yellow gel |
| 38 | D | Quab 426 (0.8) | 15500[3] | 13.5 | Clear yellow gel |
| 39 | D | E-dodecane (0.8) | — | 11.4 | Slightly hazy yellow gel |
| 40 | D | E-Hexane (0.8) | 220[6] | 11.6 | Clear yellow liquid |
| 41 | C | PSA (0.8) | — | 11.1 | Clear yellow liquid |
| 42 | B | PGE (0.8) | — | 12.9 | Hazy yellow liquid |
| 43 | A | SCA (0.8) | — | 13.9 | Clear yellow liquid |
| 44 | A | CA (1.0) | — | 13.2 | Clear yellow liquid |
| 45 | C | PEG 350 (0.3) | — | 10.1 | Clear yellow gel |
| 46 | A | Dodecenyl SA (0.3) | — | 4.3 | Slightly hazy yellow gel |
| 47 | A | Dodecenyl SA (0.8) | — | 7.4 | Slightly hazy yellow gel |
| 48 | D | Succinic Anhydride (1.0) | — | 12.8 | Clear yellow liquid |
| 49 | D | Phthalic Anhydride (0.9) | — | 12.1 | Clear yellow liquid |

[1]Based on diallylamine content

[2]Brookfield LVT #3, Speed 12 rpm

[3]Brookfield LVT #4, Speed 12 rpm

[4]Brookfield RVT-E, Speed 10 rpm

[5]Brookfield LVT #2, Speed 12 rpm

[6]Brookfield LVT A, Speed 12 rpm

Quab 151 = glycidyltrimethylammonium chloride

Quab 342 = 3-chloro-2-hydroxypropyl-dimethyldodecylammonium chloride

Quab 426 = 3-chloro-2-hydroxypropyl-dimethyloctadecylammonium chloride

E-Dodecane = 1,2-epoxydodecane

E-Hexane = 1,2-epoxyhexane

PGE = phenyl glycidyl ether

PSA = 3-chloro-2-hydroxy-1-propane sulfonic acid, Na salt

SCA = sodium chloroacetate

CA = 2-chloroacetamide

PEG 350 = Carbowax 350 = polyethylene glycol 350

Dodecenyl SA = 2-Dodecen-1-yl succinic anhydride

EXAMPLE 50

40.0 g (115.6 mmol) of perfluorobutyl iodide from Dupont, 4.1 g of deionized water and 1.1 g sodium metabisulfite (26.8% solution) are placed into a round-bottomed flask equipped with a stirrer, nitrogen inlet and a thermoregulator and heated. When the temperature reaches 60° C., 16.8 g (231.2 mmol) allyl alcohol (Acros) is added to the flask over one hour. An exotherm is observed with an increase in temperature from 60° C. to 70° C. When the rise in temperature subsides, the reaction mixture is maintained at 65° C. for three hours with stirring. At this time the consumption of perfluorobutyl iodide is determined to >95% by gas chromatography. After this time the excess allyl alcohol is removed by vacuum distillation at 85° C. The remaining mixture is cooled and transferred to a separatory funnel. 25.8 g of deionized water and 100 g of diethyl ether is added. The water layer is discarded and the ether layer dried under vacuum distillation at 40° C. The perfluoroalkyl iodide intermediate,

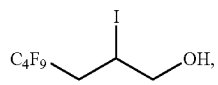

is obtained as a clear orange mixture containing 42.3% fluorine.

EXAMPLES 51-54

Table 4 summarizes the properties of grafted cationic copolymers prepared analogously to Example 29 with the grafting component of Example 50.

TABLE 4

| Example | Eg. 2 Polymer | Grafted component (Mol ratio[1]) | Solids, % | Appearance |
|---|---|---|---|---|
| 51 | A | (0.3) | 8.2 | Clear yellow liquid |
| 52 | A | (0.3) | 9.3 | Clear yellow liquid |
| 53 | C | (0.3) | 8.1 | Clear yellow liquid |
| 54 | C | (0.3) | 7.8 | Clear yellow liquid |

[1]Based on diallylamine content

Application Examples.

EXAMPLE 55

| Ingredients, wt % | Typical Range Based on Activity | 1A | 2A | 3A | 4A |
|---|---|---|---|---|---|
| Hair Conditioning Formulations | | | | | |
| Water | qs to 100% | qs to 100% | qs to 100% | qs to 100% | qs to 100% |
| Conditioning Agent | | | | | |
| Guar Hydroxypropyltrimonium Chloride | 0–2% | | | | |
| Polyquatermium-10 | 0–5% | | | | |
| Acrylamidopropyltrimonium Chloride/Acrylamide Copolymer | 0–0.5% | 0.05 | | | 0.5 |
| Copolymer of Ex. 1–54 | 0–10% | 3.0 | 1.0 | 2.0 | 5.0 |
| Thickeners | | | | | |
| Polyquaternium 37 and Mineral Oil and PPG-1 Trideceth-6 | 0–5% | 3.0 | 2.0 | | 2.5 |
| Polyquaternium 37 and Propylene Dicaprylate Dicaprate and PPG-1 Trideceth-6 | 0–5% | | | 1.0 | |
| Waxes, alcohols & emulsifiers | | | | | |
| PEG-45 Palm Kernel Glycerides | 0–5% | 0.5 | — | 1.0 | — |
| Glycereth-31 | 0–10% | 1.0 | 2.0 | — | 1.0 |
| PPG-5-Ceteth-20 | 0–5% | — | 0.5 | — | 0.5 |
| Glyceryl Stearate and PEG-100 Stearate | 0–10% | 1.0 | — | 1.5 | — |
| Cetyl Alcohol | 0–10% | 1.0 | — | 0.5 | 1.0 |
| Glycol Stearate | 0–10% | 2.0 | 1.0 | — | 2.0 |
| Ethylene Glycol Distearate | 0–10% | — | 2.0 | 1.0 | — |
| Esters/Silicones | | | | | |
| Dimethicone PEG-8 Meadowfoamate | 0–5% | — | 1.0 | 2.0 | 3.0 |
| Amodimethicone | 0–5% | | 2.0 | | |
| Vitamins | | | | | |
| Tocopherol | 0–1% | 0.1 | 0.1 | — | — |
| Panthenol | 0–1% | — | 0.1 | 0.1 | 0.1 |
| Fragrance | 0–2% | 0.5 | 0.5 | 0.5 | 0.5 |

-continued

| Ingredients, wt % | Typical Range Based on Activity | 1A | 2A | 3A | 4A |
|---|---|---|---|---|---|
| Chelating Agent | | | | | |
| Disodium EDTA | <0.10% | 0.1 | 0.1 | — | — |
| Tetrasodium EDTA | <0.10% | — | — | 0.1 | 0.1 |
| pH Adjuster | | | | | |
| NaOH | <0.50% | qs to 4.5–5.5 | qs to 4.5–5.5 | qs to 4.5–5.5 | qs to 4.5–5.5 |
| TEA | <0.50% | qs to 4.5–5.5 | qs to 4.5–5.5 | qs to 4.5–5.5 | qs to 4.5–5.5 |
| Preservative | | | | | |
| DMDM Hydantoin | 0–1% | 1.0 | 1.0 | — | — |
| Phenoxyethanol and Methylparaben and Propylparaben and Butylparaben and Isobutylparaben | 0–1% | — | — | 1.0 | 1.0 |

EXAMPLE 56

Lotion/Cream Formulation

| Ingredients, wt % | Typical Range Based on Activity | 1A | 2A | 3A | 4A |
|---|---|---|---|---|---|
| Water | qs to 100% | qs to 100% | qs to 100% | qs to 100% | qs to 100% |
| Humectant | | | | | |
| Glycerin | 0–10% | 5.0 | 2.5 | — | 4.0 |
| Propylene Glycol | 0–5% | — | 1.0 | 1.5 | 2.0 |
| Conditioner | | | | | |
| Copolymer of Ex. 1–54 | 0–5% | 2.5 | 1.0 | 5.0 | 4.0 |
| Thickening agent | | | | | |
| Carbomer | 0–1% | — | — | — | 0.8 |
| Polyacrylamide and C13–14 Isoparaffin and Laureth-7 | 0–5% | — | — | 0.8 | — |
| Acrylates/Beheneth-25 Methacrylate Copolymer | 0–5% | — | 2.5 | — | — |
| Sodium Acrylates Copolymer and Mineral Oil and PPG-1 Trideceth-6 | 0–3% | 1.0 | — | — | — |
| Emulsifiers | | | | | |
| Glyceryl Stearate | 0–5% | 3.0 | 1.0 | 1.0 | 1.5 |
| Steareth-2 | 0–5% | — | — | 0.7 | — |
| PEG-100 Stearate | 0–5% | 2.0 | — | 0.5 | — |
| Waxes | | | | | |
| Cetyl Alcohol | 0–5% | 2.0 | 1.0 | — | 1.0 |
| Cetearyl Alcohol | 0–5% | — | — | — | 1.5 |
| Stearyl Alcohol | 0–5% | — | — | 1.0 | — |
| Fatty Acids | | | | | |
| Stearic Acid | 0–10% | — | 2.5 | — | 3.0 |
| Behenic Acid | 0–10% | — | — | 1.0 | — |
| Oils/Esters | | | | | |
| Caprylic/Capric Triglyceride | 0–10% | 2.0 | 1.5 | — | 2.0 |

-continued

| Ingredients, wt % | Typical Range Based on Activity | 1A | 2A | 3A | 4A |
|---|---|---|---|---|---|
| Decyl Oleate | 0–5% | — | 0.5 | 0.8 | 1.5 |
| Cetyl Palmitate | 0–5% | 1.0 | 0.5 | — | 1.0 |
| Silicone | | | | | |
| Cyclomethicone | 0–5% | 1.0 | 1.0 | 4.0 | 2.0 |
| Dimethicone | 0–5% | — | — | — | 0.8 |
| Vitamins | | | | | |
| Tocopherol | 0–1% | 0.1 | — | 0.1 | 0.1 |
| Panthenol | 0–1% | — | 0.1 | — | 0.1 |
| Fragrance | 0–2% | 0.5 | 0.5 | 0.5 | 0.5 |
| Chelating Agent | | | | | |
| Disodium EDTA | <0.10% | 0.1 | — | 0.1 | — |
| Tetrasodium EDTA | <0.10% | | 0.1 | | 0.1 |
| pH Adjuster | | | | | |
| TEA | <0.50% | qs to 5.5–6.5 | qs to 5.5–6.5 | qs to 5.5–6.5 | qs to 5.5–6.5 |
| Preservative | | | | | |
| DMDM Hydantoin | 0–1% | — | — | 1.0 | |
| Phenoxyethanol and Methylparaben and Propylparaben and Butylparaben and Isobutylparaben | 0–1% | 1.0 | 1.0 | — | 1.0 |

We claim:

1. A functional group (Fg) containing water-soluble cationic polymer obtained by reacting (a) 0.1 to 99.9% by weight of at least one cationic base polymer of formula

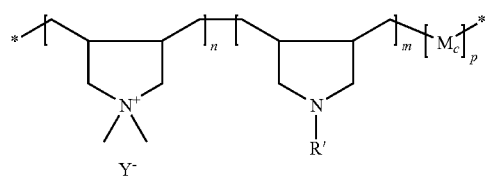

with (b) 0.1 to 99.9% by weight of at least one functional compound wherein

R' is hydrogen or $C_1$-$C_4$alkyl;

$M_c$ represents a residue from an optional monomer (C);

n, m and p are mole fractions of the repeating units of monomers (A), (B) and (C), respectively, m+n+p=1, * is a terminal group and $Y^-$ represents an anion, where the functional compound is at least one epoxy or halohydrin compound which provides the functional group Fg as

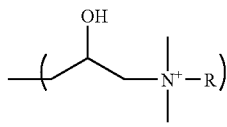

connected to at least a part of the amino groups of the base polymer, where R is hydrogen, C1 to C30 alkyl, and where the base polymer is prepared by copolymerization of at least one quaternary ammonium cationic monomer (A) and at least one monomer containing a reactive amine group (B) and optionally at least one monomer (C) other than (A) and (B), where the quaternary ammonium monomers (A) are selected from diallyldimethyl ammonium chloride, diallyldimethyl ammonium bromide, diallyldimethyl ammonium sulfates and diallyldimethyl ammonium phosphates, and where the monomers (B) are selected from diallylamines, and the weight amount of monomer A ranges from 99.8 to 50 weight percent of the base polymer.

2. A functional group containing polymer according to claim 1 of the formula

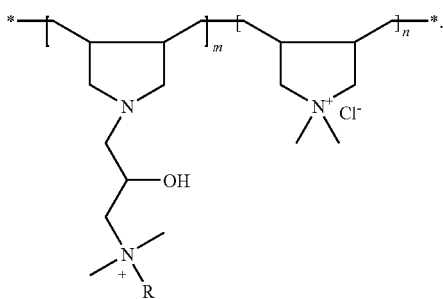

3. A functional group containing polymer according to claim 1 of the formula

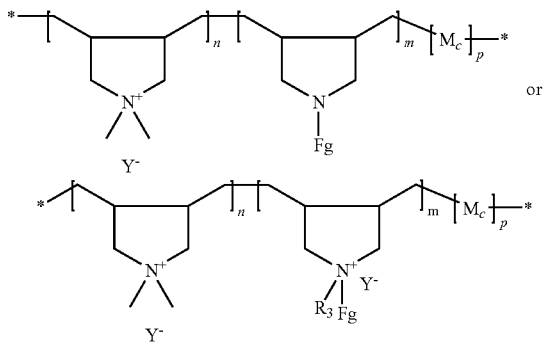

where $R_3$ is hydrogen, $C_1$-$C_4$alkyl or Fg.

4. A functional group containing polymer according to claim 1 where component (b) is 3-chloro-2-hydroxypropyl-dimethyldodecylammonium chloride or 3-chloro-2-hydroxypropyl-dimethyloctadecylammonium chloride.

5. A functional group containing polymer according to claim 1 in which at least one quaternary ammonium monomer (A) is diallyldimethyl ammonium chloride.

6. A functional group containing polymer according to claim 1, where the reactive amine group monomers (B) are selected from diallylamine, N-methyl diallylamine and N-ethyl diallylamine.

7. A functional group containing polymer according to claim 1, where the base polymer is prepared by copolymerization of at least one monomer (C) which is selected from acrylamide, methacrylamide, N,N-dimethyl acrylamide N,N-diethyl acrylamide, N,N-dimethyl aminopropyl acrylamide or salts of these monomers; acrylic acid, methacrylic acid, vinyl sulfonic acid or salts of these monomers; N,N-dimethyl aminoethyl methacrylate, N,N-dimethyl aminoethyl acrylate, diethylaminoethyl acrylate, 7-amino-3,7-dimethyloctyl acrylate or salts of these monomers; vinyl pyrrolidone, vinyl amines, vinyl formamide, vinyl alcohol, vinyl caprolactam, vinyl derivatives of dimethyl siloxane, aminosiloxanes, vinyl fluorocarbons, hydroxyalkyl acrylates and sulfur dioxide.

8. A functional group containing polymer according to claim 1 having an average molecular weight in the range of one thousand to 5 million Daltons.

9. A personal care or cosmetic composition, comprising
  A) a functional group containing cationic copolymer according to claim 1,
  B) at least one cosmetically-functional agent and
  C) at least one cosmetically tolerable adjuvant.

10. A personal care or cosmetic composition according to claim 9, wherein the functional group containing cationic polymer is of formula

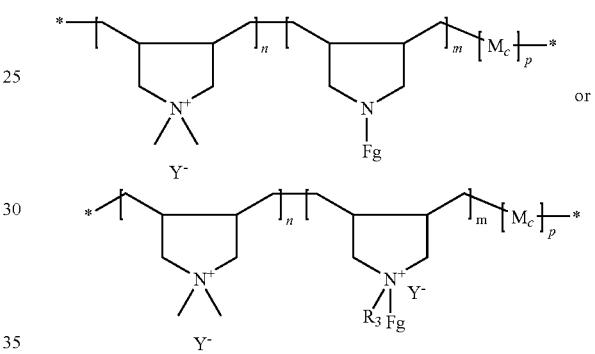

where $R_3$ is hydrogen, $C_1$-$C_4$alkyl or Fg.

11. A personal care composition according to claim 9, which is a hair conditioning product and wherein the cosmetically-functional agent is an effective amount of one or more surfactants.

12. A hair conditioning product according to claim 11, further comprising at least one cosmetically tolerable adjuvant selected from softeners, perfumes, colorants, preservatives, antimicrobials, optical brighteners, ultraviolet light absorbers, other light management agents and mixtures thereof.

* * * * *